(12) United States Patent
Looft et al.

(10) Patent No.: US 8,487,133 B2
(45) Date of Patent: Jul. 16, 2013

(54) SUBSTITUTED BICYCLO [4.1.0] HEPTANE-7-CARBOXYLIC ACID AMIDES AND DERIVATIVES THEREOF AS FOOD FLAVOR SUBSTANCES

(75) Inventors: Jan Looft, Holzminden (DE); Tobias Vössing, Beverungen (DE); Michael Backes, Holzminden (DE)

(73) Assignee: Symrise AG, Holzminden (DE)

( * ) Notice: Subject to any disclaimer, the term of this patent is extended or adjusted under 35 U.S.C. 154(b) by 769 days.

(21) Appl. No.: 12/445,842

(22) PCT Filed: Oct. 18, 2007

(86) PCT No.: PCT/EP2007/061171
§ 371 (c)(1),
(2), (4) Date: Apr. 8, 2010

(87) PCT Pub. No.: WO2008/046895
PCT Pub. Date: Apr. 24, 2008

(65) Prior Publication Data
US 2010/0189863 A1    Jul. 29, 2010

Related U.S. Application Data

(60) Provisional application No. 60/829,958, filed on Oct. 18, 2006.

(51) Int. Cl.
C07C 233/58    (2006.01)
(52) U.S. Cl.
USPC .......................................... 564/188; 426/538
(58) Field of Classification Search
USPC .......................................... 564/188; 426/538
See application file for complete search history.

(56) References Cited

U.S. PATENT DOCUMENTS

| | | | |
|---|---|---|---|
| 3,504,080 A * | 3/1970 | Rein et al. | 264/235 |
| 4,331,570 A * | 5/1982 | Klemarczyk et al. | 512/17 |
| 4,386,064 A * | 5/1983 | Klemarczyk et al. | 424/49 |
| 2004/0077617 A1 | 4/2004 | Bennani et al. | |
| 2004/0209859 A1* | 10/2004 | Bennani et al. | 514/183 |
| 2006/0057268 A1 | 3/2006 | Dewis et al. | |

FOREIGN PATENT DOCUMENTS
WO    WO-2004075663    9/2004

OTHER PUBLICATIONS

Drake, Nathan L. et al.: "The reaction of phenanthrene with ethyl diazoacetate" Journal of Organic Chemistry, vol. 11, 1946, pp. 67-74, XP009094717 p. 72, lines 13-16; figure IV.

Ganellin, C.R.: "Homologization of phenanthrene by diazomethane" Tetrahedron Letters, vol. 39-40, 1964, pp. 2919-2923, XP009094712, p. 1920, paragraph 2; figure IVc.

Buchner E and Weigand W: "Bornylen und Diazoessigester" Chemische Berichte, vol. 46, 1913, pp. 2108-2117, XP002465301, p. 2116, line 9-line 16; figure II.

Sauers, R.R. et al: "Synthesis and chemistry of some tricyclo [4.2.1. 02,5]nonane derivatives" Journal of Organc Chemistry, vol. 33, No. 6, 1968, pp. 2175-2181, XP009094720, p. 2179, left-hand column; figure 17.

Olteanu E: "The Synthesis and the decomposition of benzonorbornane annelated with methyl(cyclopropylcarbinyl)-N-nitrosourethane," Revue Roumaine De Chimie, vol. 51, No. 7-8, 2006, pp. 663-668, XP009094787, p. 665, last paragraph-p. 666, paragraph 4; figure 9.

Lebel, Norman A. et al.: "Tetracyclo[3.3.0.02,8.04,6]octan-3-one. Preparation, characterization, and physical and chemical properties" Journal of the American Chemical Society, vol. 87, No. 19, 1965, pp. 4301-4309, XP009094721; figure 23.

* cited by examiner

*Primary Examiner* — Shailendra Kumar
(74) *Attorney, Agent, or Firm* — Novak Druce Connolly Bove + Quigg LLP

(57) ABSTRACT

The present invention relates to the use of a compound of the Formula (I)

(I)

wherein:
$R^1$, $R^2$, $R^3$, $R^4$, $R^5$, $R^6$, $R^7$ and $R^8$ denote in each case independently of one another hydrogen, an alkyl radical with 1 to 6 C atoms, or an alkenyl radical with 2 to 6 C atoms,
with the proviso that at least one of the radicals $R^1$, $R^2$, $R^7$ and $R^8$ and at least one further of the radicals $R^1$, $R^2$, $R^3$, $R^4$, $R^5$, $R^6$, $R^7$ and $R^8$ are not hydrogen, wherein independently of one another also two of the radicals $R^1$, $R^2$, $R^3$, $R^4$, $R^5$, $R^6$, $R^7$ and $R^8$ can together denote a bridge with one or more bridge C atoms;
$Y^1$ and $Y^2$ denote independently of one another hydrogen, methyl or ethyl;
and
$R^a$ and $R^b$ denote independently of one another hydrogen, an alkyl radical with 1 to 6 C atoms, an alkenyl radical with 2 to 6 C atoms or a cycloalkyl radical with 3 to 6 C atoms as a food flavor substance.

10 Claims, 3 Drawing Sheets

SUBSTITUTED BICYCLO [4.1.0] HEPTANE-7-CARBOXYLIC ACID AMIDES AND DERIVATIVES THEREOF AS FOOD FLAVOR SUBSTANCES

CROSS-REFERENCE TO RELATED APPLICATIONS

This application claims benefit of priority to PCT/EP2007/061171, filed on Oct. 18, 2007, which asserts priority to U.S. Provisional Application No. 60/829,958, filed on Oct. 18, 2006, which are incorporated herein by reference in their entireties.

The present invention relates to the use of specific substituted bicyclo[4.1.0]heptane-7-carboxylic acid amides and specific derivatives thereof of the Formula (I) (see below) as food flavor substances (taste substances). The compounds are suitable in particular for producing, modifying or intensifying an umami flavor. The invention relates furthermore to specific compositions and semi-finished products which contain a flavor-imparting effective amount of the aforementioned compounds of the Formula (I), as well as specific methods for producing, modifying and/or intensifying specific flavor impressions, in particular the umami taste. Finally, the invention also relates to new compounds of the Formula (I) (see below) that impart special flavor impressions.

Aroma substances and compounds with unusual sensorial properties, which carry an amide group, have been known for some time. Thus, for example, many important cooling substances such as WS3, WS5 and WS23 have an amide structure:

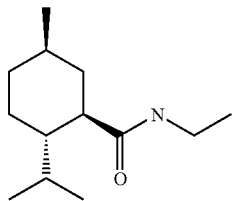

WS3

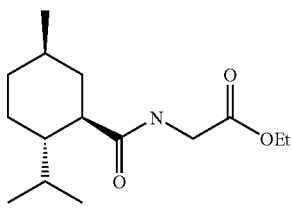

WS5

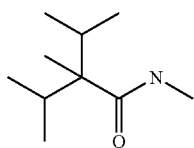

WS23

Sensorially important amides also include the hot-tasting substances capsaicin from Chili pods and the piperin of white pepper. The naturally occurring alkamides pellitorin and spilanthol have, apart from a saliva-generating and tingling action, also a long-lasting and numbing effect in the mouth:

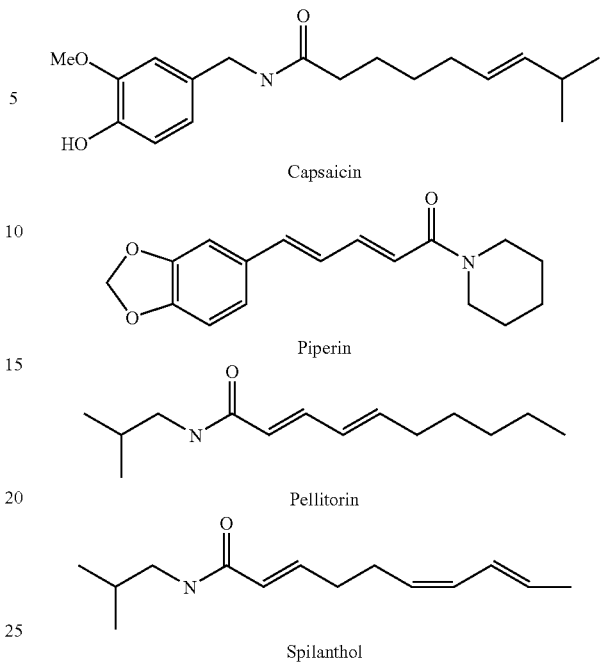

Based on the chemical structure of spilanthol, various alkylidene amides have been proposed in US 2004/0202760 and US 2004/0202619, which include quite different sensorial impressions such as tingling, numbing, acerbity, sensation of fullness in the mouth (mouthfeel), etc. For some compounds such as N-cyclopropyl-E2,Z6-nonadiene amide, N-ethyl-E2,Z6-dodecadiene amide and N-ethyl-E2,Z6-nonadiene amide an MSG-like action (MSG=monosodium glutamate, sodium glutamate) and/or an umami-like impression are also mentioned.

In the documents US 2006/0068071/EP 1642886/US 2006/0057268 saturated, unsaturated and cyclopropyl-N-alkylamides are disclosed, which are said to have taste-promoting or aroma-promoting actions.

A large number of allegedly flavor-active non-natural amides are described in the publication US 2005/084506 A1.

Several publications, listed in the following table, are concerned with the synthesis of bicyclo[4.1.0]heptane-7-carboxylic acid amides of the structure shown below.

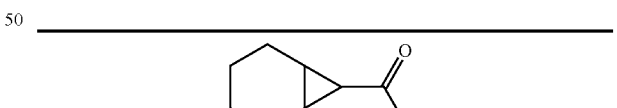

| Radical R1 | Literature |
|---|---|
| H₂N— | Hans Musso, Chem. Berichte (1968), 101(11), 3710-3720. |
| H₂N— | Donald B. Denny et al., J. Am. Chem Soc. (1962), 84, 3944-3946. |
| Me₂N— | Michael P. Doyle et al., Tetrahedron Letters 1987, 28(8), 833-836. |
| Et₂N— | Toshikazu Hirao et al., Tetrahedron Letters (1985), 26(41), 5061-5064. |
| H₂N—NH— | I. A. Dýakonov et al., Zhurnal Obshchei Khimii (1967), 3(8), 141-148. |
| H₂N—NH— | I. G. Bolesov et. al., Zhurnal Organicheskoi Khimii (1974), 10(10), 2107-2113. |

-continued

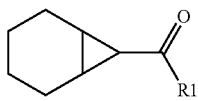

| Radical R1 | Literature |
|---|---|
| PhHN— | P. Besinet et al., Bulletin de la Societe Chimique de France (1969), 1377-1381. |
| PhHN— | Max Mousseron, Compt. rend. (1956), 243, 1880-1882. |

In this connection Me denotes methyl, Et denotes ethyl and Ph denotes phenyl.

Alkylamides where R1=NH-alkyl are not disclosed in the above publications.

Several documents describe bicyclo[4.1.0]heptane-7-carboxylic acid amides as having biological or pharmacological actions. These are in particular the following documents:

WO 2004/032716: Modulation of cholesterol transport by regulating the HDL Scavenger Receptor SR-BI.

The following compound with a bicyclo[4.1.0]heptane-7-carboxylic acid amide structure is specified:

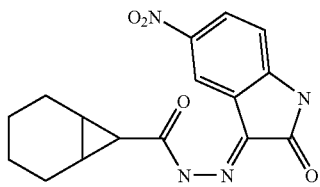 [SMILES: O=C1Nc2ccc([N+](=O)[O-])cc2/C1=N\NC(=O)C1C2CCCCC21]

U.S. Pat. No. 5,123,951: Plant growth regulators.

The following compound with a bicyclo[4.1.0]heptane-7-carboxylic acid amide structure is specified:

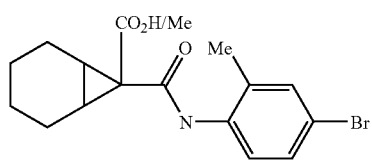

WO 2005/007141: Inhibitors of the POSH ubiquitin ligase for the treatment of neurological and viral diseases and cancer.

The following compound with a bicyclo[4.1.0]heptane-7-carboxylic acid amide structure is specified:

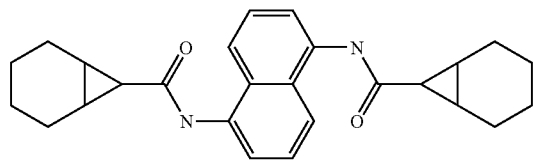 [SMILES: O=C(Nc1cccc2c(NC(=O)C3C4CCCCC43)cccc12)C1C2CCCCC21]

Two literature references describe bicyclo[4.1.0]heptane-7-carboxylic acid amides, which are substituted with two alkyl substituents on the bicyclic skeleton. In particular the following patent is one of the references:

US 2004/209859 discloses the use of di-substituted and tri-substituted bicyclo[4.1.0]heptane-7-carboxylic acid derivatives as anticonvulsive compounds used inter alia for the treatment of migraine, epilepsy or dipolar disorders.

In this connection the following general formula is given for the active class of compounds:

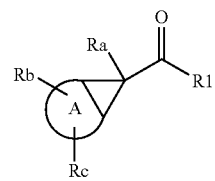

wherein:

A denotes cycloalkyl or bicycloalkyl

Ra, Rb, Rc denote independently of one another H or alkyl

R1 denotes OR2 or NR3R4 where R2 denotes H or alkyl, and R3, R4 independently of one another denote for example H, alkyl or alkenyl.

Examples of amides covered by the general formula are listed as individual compounds:

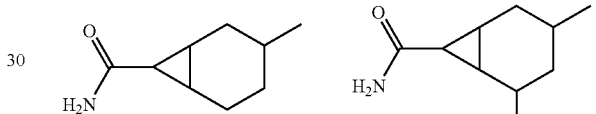

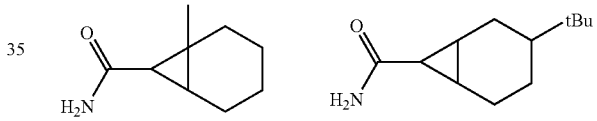

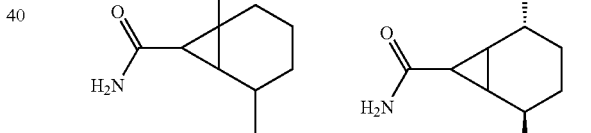

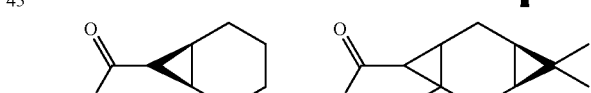

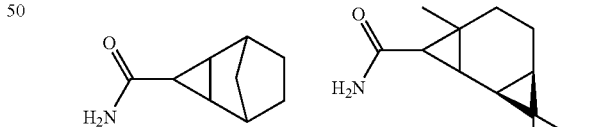

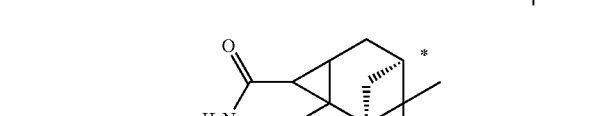

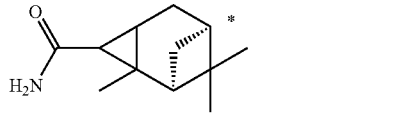

A

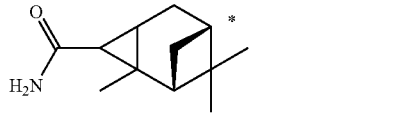

B

-continued

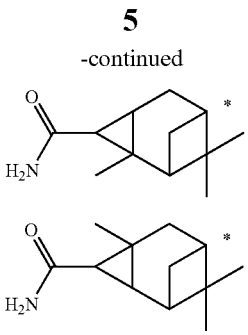

C

D

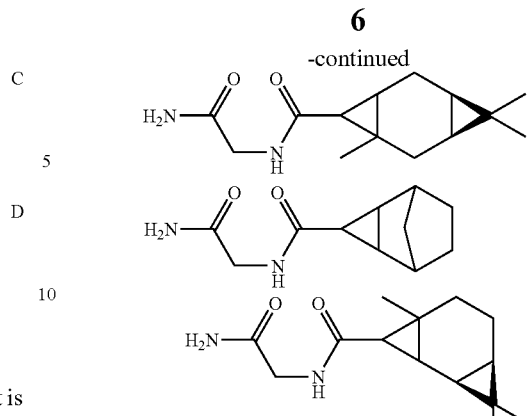

A'

B'

C'

D'

*: with each of the compounds identified by an asterisk *, it is not clear whether this is actually disclosed in the document US 2004/209859. In the heading to Example 38 of the publication 2,7,7-trimethyl-tricyclo[4.1.1.02,4]octane-3-carboxylic acid amide (C) is for example mentioned; the product of the described synthesis is however (1S,6R)-2,7,7-trimethyltricyclo[4.1.1.02,4]octane-3-carboxylic acid amide (A). In the heading to Example 49, 4,7,7-trimethyltricyclo[4.1.1.02,4]octane-3-carboxylic acid amide (D) is mentioned; the product of the described synthesis is however (1R,6S)-2,7,7-trimethyl-tricyclo[4.1.1.02,4]octane-3-carboxylic acid amide (B).

Furthermore, the analogous derivatives in the form of the amides of glycinamide are listed as individual compounds:

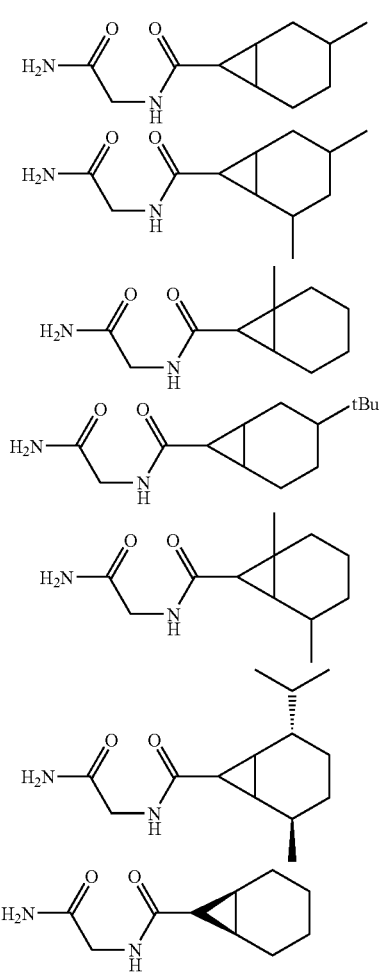

*: In the case of each of the compounds identified by an asterisk * it is not clear whether this is actually disclosed in the document US 2004/209859. In the heading to Example 39 of the publication N-(2-amino-2-oxoethyl)-2,7,7-trimethyl-tricyclo[4.1.1.02,4]octane-3-carboxylic acid amide (C') for example is mentioned; the product of the described synthesis is however (1S,6R)—N-(2-amino-2-oxoethyl)-2,7,7-trimethyltricyclo[4.1.1.02,4]octane-3-carboxylic acid amide (A'). In the heading to Example 50 N-(2-amino-2-oxoethyl)-4,7,7-trimethyltricyclo[4.1.1.02,4]octane-3-carboxylic acid amide (D') is mentioned; the product of the described synthesis is however (1R,6S)—N-(2-amino-2-oxoethyl)-2,7,7-trimethyltricyclo[4.1.1.02,4]octane-3-carboxylic acid amide (B').

Jeganathan et al. describe in J. Org. Chem. 1986, 51, 5362-5367 the addition of N-(4-azidophenyl)-1-diazoacetamides to dialkyl-substituted cyclohexenes. The bicyclo[4.1.0]heptane-7-carboxylic acid amides formed thereby have, as N-aryl amides, the following structure:

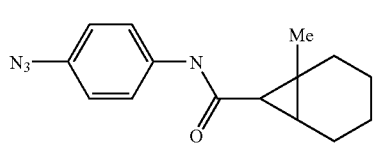 [SMILES: CC12CCCCC1C2C(=O)Nc1ccc(N=[N+]=[N-])cc1]

The flavor of bicyclo[4.1.0]heptane-7-carboxylic acid amides (and their derivatives, i.e. substituted or unsubstituted) has not up to now been mentioned in any literature reference.

There is furthermore a need to discover new food flavor substances and aroma substances, flavor-active compounds, or compounds which can produce, modify or intensify an aroma. In particular there is a need for those compounds which can produce or intensify the "umami" flavor impression.

In the search for such compounds it was surprisingly found that specific substituted bicyclo[4.1.0]heptane-7-carboxylic acid alkylamides of the Formula (I) (see below) are strong food flavor substances.

A first aspect of the present invention therefore relates to the use of a compound of the Formula (I)

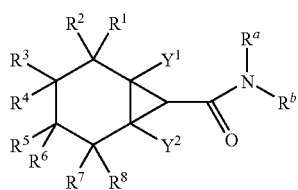

(I)

wherein:
R1, R2, R3, R4, R5, R6, R7 and R8 denote in each case independently of one another hydrogen, an alkyl radical with 1 to 6 C atoms, or an alkenyl radical with 2 to 6 C atoms,
with the proviso that at least one of the radicals R1, R2, R7 and R8 and at least a further one of the radicals R1, R2, R3, R4, R5, R6, R7 and R8 are not hydrogen, wherein independently of one another also two of the radicals R1, R2, R3, R4, R5, R6, R7 and R8 can together denote a bridge with one or more bridge C atoms;
Y1 and Y2 denote independently of one another hydrogen, methyl or ethyl, preferably hydrogen or methyl, particularly preferably both denote hydrogen;
and
Ra and Rb denote independently of one another hydrogen, an alkyl radical with 1 to 6 C atoms, an alkenyl radical with 2 to 6 C atoms or a cycloalkyl radical with 3 to 6 C atoms
as a food flavor (taste) substance.

Preferably in this connection three, four, five or six of the radicals R1, R2, R3, R4, R5, R6, R7 and R8 denote hydrogen.

The total number of carbon atoms of a compound of the Formula (I) used according to the invention is preferably not greater than 25, preferably not greater than 20.

According to a modification of the use according to the invention it is preferred if the compound of the Formula (I) comprises in each case hydrogen as radicals R2, R4, R6 and R8 and is thus a compound of the Formula (II)

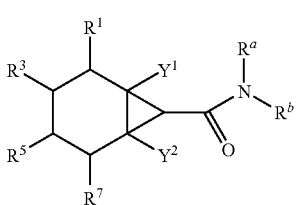

(II)

wherein;
R1, R3, R5 and R7 denote in each case independently of one another hydrogen, an alkyl radical with 1 to 6 C atoms or an alkenyl radical with 2 to 6 C atoms,
with the proviso that at least 1 of the radicals R1 and R7 and a further one of the radicals R1, R3, R5 and R7 are not hydrogen,
wherein independently of one another also two of the radicals R1, R3, R5 and R7 may jointly form a bridge with one or more bridge C atoms,
Y1 and Y2 denote independently of one another hydrogen, methyl or ethyl,
and
Ra and Rb denote independently of one another hydrogen, an alkyl radical with 1 to 6 C atoms, an alkenyl radical with 2 to 6 C atoms or a cycloalkyl radical with 3 to 6 C atoms.

With regard to the preferred compounds of the Formula (II) used according to the invention, the comments made above with regard to the compounds of the Formula (I) apply.

It is preferred to use a compound of the Formula (I) (preferably of the Formula (II)), in particular one of the preferred compounds described above and hereinafter, for producing, modifying or intensifying an umami taste.

The cyclopropanecarboxylic acid ethylamide not according to the invention and illustrated hereinafter has, as our own investigations have shown, a very weak umami taste at concentrations of 10 ppm in aqueous solutions.

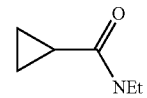

However, in sensorial tests the compound does not make any statistically significant contribution to the mouthfeel, as our own tests with meat broth/consommé compositions have established.

The unsubstituted bicyclo[4.1.0]heptane-7-carboxylic acid ethylamide not according to the invention has no detectable taste (the following drawing shows the numbering of the positions on the basic skeleton):

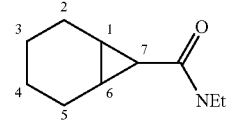

By simply adding a single alkyl substituent the resulting compound, not according to the invention, has a slight sensorial activity, as our own investigations have shown. Thus, for example, 2-isopropyl-bicyclo[4.1.0]heptane-7-carboxylic acid ethylamide has a slight salt-intensifying effect and a very slight, umami-like intrinsic taste:

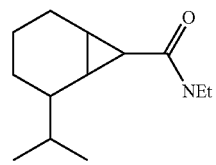

It has now surprisingly been found however that the sensorial effects are significantly increased by a second alkyl substituent. The 2,4-dimethyl-bicyclo[4.1.0]heptane-7-carboxylic acid ethylamide according to the invention also has, like the just discussed mono alkyl-substituted compound, a slight salt-intensifying effect, but on the other hand has a stronger, umami-like intrinsic taste:

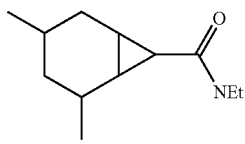

An important factor for the sensorial effectiveness of a compound of the Formula (I) is generally the position of the substituents. In our own investigations di-substituted compounds of the Formula (I) with substituents on the 2 and 4 positions or on the 2 and 5 positions have proved particularly advantageous.

A use according to the invention of a compound of the Formula (I) is therefore preferred, in which the compound of the Formula (I) is
a compound of the Formula (III),

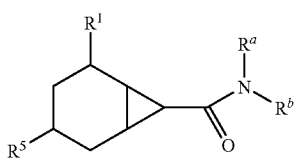

wherein:
R1 and R5 denote independently of one another in each case an alkyl radical with 1 to 6 C atoms or jointly denote a bridge with one or more bridge C atoms,
or
   is a compound of the Formula (IV)

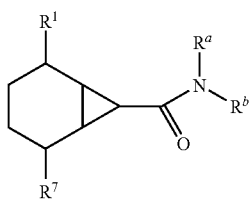

wherein:
R1 and R7 denote independently of one another in each case an alkyl radical with 1 to 6 C atoms or jointly denote a bridge with one or more bridge C atoms,
wherein in Formula (III) and Formula (IV):
Ra and Rb denote independently of one another hydrogen, an alkyl radical with 1 to 6 C atoms, an alkenyl radical with 2 to 6 C atoms or a cycloalkyl radical with 3 to 6 C atoms.

Preferably in this connection R1 and R5 in Formula (III) as well as R1 and R7 in Formula (IV) denote independently of one another in each case methyl, ethyl, n-propyl, iso-propyl, n-butyl, iso-butyl, sec-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methyl-pentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl or 1,2,2-trimethylpropyl,
or jointly denote a —CH$_2$—, —C(Me)2-, —CH2CH2- or —CH═CH—-bridge.

With a compound according to the invention compounds of the Formula (III) or (IV) are preferred, in which Ra and Rb independently of one another denote hydrogen or an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl
or denote an alkenyl radical with 2 to 6 C atoms,
or denote a cycloalkyl radical with 3 to 6 C atoms,
wherein preferably Rb denotes ethyl, cyclopropyl, cyclobutyl, cyclopentyl or cyclohexyl.

Particularly preferred is the use according to the invention of compounds of the Formula (III) or (IV) in which
Ra denotes hydrogen
and
Rb denotes an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl,
or denotes an alkenyl radical with 2 to 6 C atoms or denotes a cycloalkyl radical with 3 to 6 C atoms, preferably ethyl, cyclopropyl, cyclobutyl, cyclopentyl or cyclohexyl
or
Ra and Rb both denote methyl.

Tricyclo[3.2.1.02,4]octane-3-carboxylic acid ethylamide has a distinct umami taste and a salt-intensifying effect. In sensorial tests a statistically significant increase in the mouthfeel is found already at concentrations of 50 ppm in broths/consommés made from American beef extract:

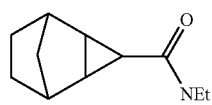

In sensorial tests it has been found that the relative configuration of the stereocenters has a large influence on the taste properties of compounds of the Formula (I). From the taste aspect the use according to the invention of a compound of the Formula (I) which is one of the two enantiomeric compounds of the Formula (IVa),

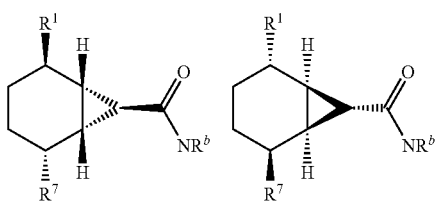

(IVa)

is in particular preferred.

As regards the preferred meanings of the substituents R1, R7 and Rb the comments made above apply as appropriate.

2-Isopropyl-5-methyl-2-ispropyl-bicyclo[4.1.0]heptane-7-carboxylic acid ethylamide has particularly strong sensorial properties. In this connection the relative configuration of the stereogenic centers is of great importance. The compound with the absolute stereo-chemistry (as shown in the following structural formula) (1S,2S,5R,6R,7S)-2-isopropyl-5-methyl-bicyclo[4.1.0]heptane-7-carboxylic acid ethylamide has a slight cooling effect in sensorial tests, but tastes only moderately of umami:

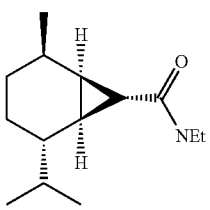

(IVb)

In contrast to this the diastereomeric compound (1R,2S,5R,6S,7R)-2-isopropyl-5-methyl-bicyclo[4.1.0]heptane-7-carboxylic acid ethylamide (Formula (IVc)) has no cooling effect, but has a very strongly pronounced intrinsic umami taste:

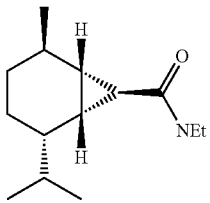

(IVc)

This compound of the Formula (IVc) also intensifies the saltiness, the sweetness and the umami taste of aroma compositions. In our own investigations a trained panel found, again in a statistically significant manner, that simply by adding 5 ppm of the compound to 0.5 wt. % of American beef bouillon, the mouthfeel is increased by roughly the same extent as is normally achieved only by the addition of 0.05 wt. % of MSG.

A mixture of both diastereomers specified above, which can be obtained for example as the product of a synthesis starting from (+)-p-menth-(2)-ene, is completely dominated by the umami impression of the (1R,2S,5R,6S,7R) isomer, and by comparison the cooling impression can no longer be detected.

For this reason a diastereomeric mixture was employed in each case for the further sensorial evaluations.

In further investigations it was found that also a mixture of the two diastereomers (1R,2R,5S,6S,7R)-2-isopropyl-5-methyl-bicyclo[4.1.0]heptane-7-carboxylic acid ethylamide (E1) and (1S,2R,5S,6R,7S)-2-isopropyl-5-methyl-bicyclo[4.1.0]heptane-7-carboxylic acid ethylamide (E2), which are enantiomeric to (IVb) and (IVc), have an intrinsic umami taste.

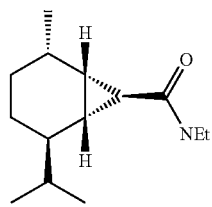

(E1)

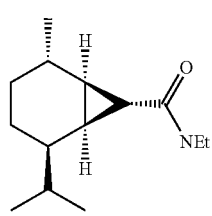

(E2)

By varying the amine used it was surprisingly found that the corresponding compounds of cyclobutylamine (B1) and (B2), cyclopentylamine (P1) to (P4) and cyclohexylamine (H1) and (H2) likewise have a very strongly pronounced intrinsic umami taste.

With a mixture of the two diastereomers (1S,2S,5R,6R,7S)-2-isopropyl-5-methyl-bicyclo[4.1.0]heptane-7-carboxylic acid cyclobutylamide (B1) and (1R,2S,5R,6S,7R)-2-isopropyl-5-methyl-bicyclo[4.1.0]heptane-7-carboxylic acid-cyclobutylamide (B2), apart from a very strong umami note a slightly sweetish impression was also noted.

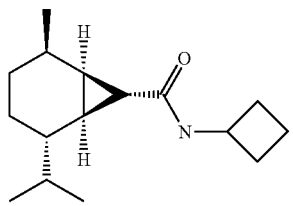

(B1)

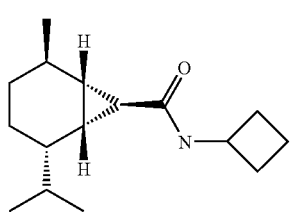

(B2)

With a mixture of the two diastereomers (1S,2S,5R,6R,7S)-2-isopropyl-5-methyl-bicyclo[4.1.0]heptane-7-carboxylic acid cyclopentylamide (P1) and (1R,2S,5R,6S,7R)-2-isopropyl-5-methyl-bicyclo[4.1.0]heptane-7-carboxylic acid cyclopentylamide (P2) a very much more intensive and clear umami taste was detected at very low concentrations.

(P1)

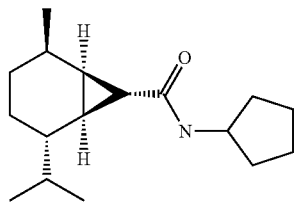

(P2)

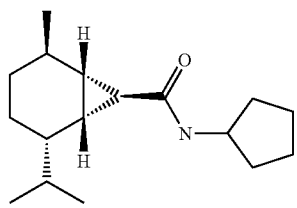

Also, a mixture of the diastereomers (1R,2R,5S,6S,7R)-2-isopropyl-5-methyl-bicyclo[4.1.0]heptane-7-carboxylic acid cyclopentylamide (P3) and (1S,2R,5S,6R,7S)-2-isopropyl-5-methyl-bicyclo[4.1.0]heptane-7-carboxylic acid cyclopentylamide—prepared from $(-)_p$-meth-(2)-ene—which are enantiomeric to (P1) and (P2), exhibited a very strongly pronounced umami taste.

(P3)

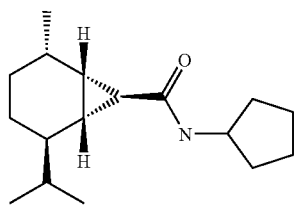

(P4)

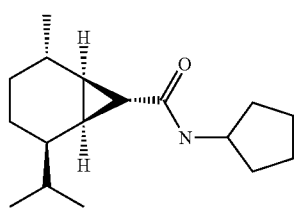

With a mixture of the two diastereomers (1S,2S,5R,6R,7S)-2-isopropyl-5-methyl-bicyclo[4.1.0]heptane-7-carboxylic acid cyclohexylamide (H1) and (1R,2S,5R,6S,7R)-2-isopropyl-5-methyl-bicyclo[4.1.0]heptane-7-carboxylic acid-cyclohexylamide (H2) an umami note was also detected, which however developed somewhat more slowly.

(H1)

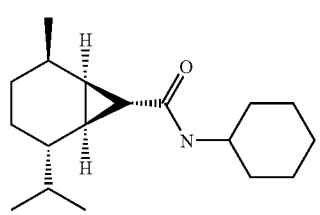

(H2)

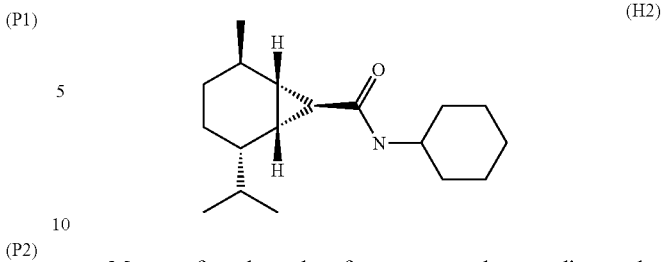

Most preferred are therefore compounds according to the invention of the Formulae (IVc), (E), (B), (P) and (H), as well as arbitrary mixtures of these substances with one another as well as mixtures with the diastereomers (e.g. IVb) occurring during their synthesis. (E) is understood to denote all above mentioned compounds of the corresponding group (in this case (E1) and (E2)). The comments made as regards (E) apply as appropriate to (B) (in this case to (B1) and (B2)), (P) (in this case to (P1), (P2), (P3) and (P4)) and (H) (in this case to (H1) and (H2)).

Compared to other compounds having an umami taste, (1R,2S,5R,6S,7R)-2-isopropyl-5-methyl-bicyclo[4.1.0]heptane-7-carboxylic acid ethylamide (IVc), the mixture of (1S,2S,5R,6R,7S)-2-isopropyl-5-methyl-bicyclo[4.1.0]heptane-7-carboxylic acid cyclobutylamide (B1) and (1R,2S,5R,6S,7R)-2-isopropyl-5-methyl-bicyclo[4.1.0]heptane-7-carboxylic acid cyclobutylamide (B2) as well as the mixture of (1S,2S,5R,6R,7S)-2-isopropyl-5-methyl-bicyclo[4.1.0]heptane-7-carboxylic acid cyclopentylamide (P1) and (1R,2S,5R,6S,7R)-2-isopropyl-5-methyl-bicyclo[4.1.0]heptane-7-carboxylic acid cyclopentylamide (P2) are characterized by a clear umami taste very similar to sodium glutamate (MSG). This is also illustrated in the accompanying spider diagrams, in which an American beef bouillon as base is compared firstly to such a base containing an addition of 5 ppm of (1R,2S,5R,6S,7R)-2-isopropyl-5-methyl-bicyclo[4.1.0]heptane-7-carboxylic acid ethylamide (IVc) (FIG. 1) or 2 ppm of a mixture of (1S,2S,5R,6R,7S)-2-isopropyl-5-methyl-bicyclo[4.1.0]heptane-7-carboxylic acid cyclobutylamide (B1) and (1R,2S,5R,6S,7R)-2-isopropyl-5-methyl-bicyclo[4.1.0] heptane-7-carboxylic acid cyclobutylamide (B2) (FIG. 2) or 0.5 ppm of a mixture of (1S,2S,5R,6R,7S)-2-isopropyl-5-methyl-bicyclo[4.1.0]heptane-7-carboxylic acid cyclopentylamide (P1) and (1R,2S,5R,6S,7R)-2-isopropyl-5-methyl-bicyclo[4.1.0]heptane-7-carboxylic acid-cyclopentylamide (P2) (FIG. 3) respectively, and secondly with such a base containing an addition of 0.05 wt. % of MSG.

In our own investigations it has been shown that the compounds of the Formulae (I), (II), (III) or (IV) used according to the invention in foods with a greatly reduced sodium glutamate content or free of sodium glutamate, thus for example in spicy foods such as tomato soup, chicken soup, snacks/nibbles, oven-ready pizzas, potato crisps and popcorn can produce, modify and/or intensify extremely well an umami taste both in the initial taste (impact) as well as in the longer-lasting taste perception, and the taste experience is therefore perceived as pleasant and in many cases is even preferred.

According to a further aspect the present invention also relates to compositions, in particular compositions suitable for consumption, including or consisting of a flavor-effective amount of one or more compounds of the Formulae (I), (II), (III) or (IV) as well as one or more further constituents (ingredients) suitable for consumption. As regards the compounds of the Formula (I) used according to the invention and contained in the composition, which is preferably a compound of the Formula (II), (III) or (IV), the comments made above apply as appropriate.

The preparations (compositions) according to the invention used for nutritional, oral hygiene or consumption purposes are normally products that are intended to be ingested orally, where they remain in the mouth for a certain time and are then either consumed (for example foodstuffs ready for consumption, see also hereinafter) or are removed from the mouth (for example chewing gums or toothpastes). These products thus include all substances or preparations that are intended to be ingested in the processed, partially processed or unprocessed state by humans. These products in addition also include substances that are added to foodstuffs in the course of their preparation, processing or treatment and are accordingly intended to be ingested by humans.

Within the context of the present specification "foodstuffs" are understood in particular to be substances which are intended to be swallowed in the unaltered, prepared or processed state by humans and then digested; foodstuffs are also understood to include coatings, coverings or other types of enclosures which are intended to be swallowed at the same time, or in which swallowing is envisaged. Also, certain products that are normally removed from the mouth (e.g. chewing gums) are understood to be foodstuffs within the context of the present specification, since it is not out of the question that they are at least partially swallowed.

A foodstuff that is ready for consumption is understood in this connection to mean a foodstuff that is already fully formulated as regards the substances important for the taste and flavor. The term "foodstuff ready for consumption" also includes beverages, drinks as well as solid or semi-solid foodstuffs ready for consumption. Examples that may be mentioned include deepfrozen products that have to be defrosted before consumption and heated to the consumption temperature. Also, products such as yoghurt or ice-cream and also chewing gum or hard caramels are included as foodstuffs ready for consumption.

A mouth care product (also termed oral hygiene product or oral hygiene preparation) within the context of the invention is one of the formulations known to the person skilled in the art for cleaning and care of the oral cavity and throat and also for freshening the breath. Dental care and gum care is specifically included in this connection. Application forms of conventional oral hygiene formulations are in particular crèmes, gels, pastes, foams, emulsions, suspensions, aerosols, sprays as well as capsules, granules, pastilles, tablets, sweets or chewing gum, though this list should not be understood as limiting for the purposes of the present invention.

Preferred mouthcare products (oral hygiene products) are in particular those in the form of toothpastes, dental crèmes, dental gels, dental powders, dental cleaning liquids, dental cleaning foams, mouthwashes, dental crèmes and mouthwashes as two-in-one products, lollypops, mouth sprays, flossing agents or dental chewing gums.

Chewing gums include in general a chewing gum base, i.e. a chewing composition that becomes plastic on chewing, sugars of various types, sugar substitutes, other sweeteners, sugar alcohols (in particular sorbitol, xylitol, manitol), cooling substances, taste corrigents for unpleasant taste impressions, further taste-altering substances (for example inositol phosphate, nucleotides such as guanosine monophosphate, adenosine monophosphate or other substances such as sodium glutamate or 2-phenoxypropionic acid), humectants, thickening agents, emulsifiers, stabilizers, odor corrigents and aroma substances (e.g.: eucalyptus-menthol, cherry, strawberry, grapefruit, vanilla, banana, citrus fruits, peach, blackcurrant, tropical fruits, ginger, coffee, cinnamon, combinations (of the aforementioned aroma substances) with mint aromas such as spearmint and peppermint alone). The combination of the aroma substances with further substances that have cooling, warming and/or mouth-watering properties is also of particular interest In the prior art numerous different chewing gum bases are known, in which connection a distinction should be made between so-called "chewing gum" bases and "bubble gum" bases, the latter being softer so that bubbles of chewing gum can also be produced. Common chewing gum bases include, apart from traditionally used natural resins or chicle from natural latex, nowadays generally elastomers such as polyvinyl acetates (PVA), polyethylenes, (low molecular weight or medium molecular weight) polyisobutenes (PIB), polybutadienes, isobutene-isoprene copolymers (butyl rubber), polyvinyl ethyl ether (PVE), polyvinyl butyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the aforementioned elastomers, as described for example in EP 0 242 325, U.S. Pat. No. 4,518,615, U.S. Pat. No. 5,093, 136, U.S. Pat. No. 5,266,336, U.S. Pat. No. 5,601,858 or U.S. Pat. No. 6,986,709. In addition chewing gum bases include further constituents such as for example (mineral) fillers, plasticizers, emulsifiers, antioxidants, waxes, fats or fatty oils, such as for example hardened (hydrogenated) vegetable or animal fats, and monoglycerides, diglycerides or triglycerides. Suitable (mineral) fillers are for example calcium carbonate, titanium dioxide, silicon dioxide, talcum, aluminium oxide, dicalcium phosphate, tricalcium phosphate, magnesium hydroxide and their mixtures. Suitable plasticizers and agents for preventing agglutination (detackifiers) are for example lanolin, stearic acid, sodium stearate, ethyl acetate, diacetin (glycerol diacetate), triacetin (glycerol triacetate), triethyl citrate. Suitable waxes are for example paraffin waxes, candelilla wax, carnauba wax, microcrystalline waxes and polyethylene waxes. Suitable emulsifiers are for example phosphatides such as lecithin, monoglycerides and diglycerides of fatty acids, e.g. glycerol monostearate.

A number of compositions according to the invention are preferred. Particularly preferred is a (preferably spray-dried) composition which includes, in addition to one or more compounds of the Formulae (I), (II), (III) or (IV) used according to the invention, also one or more solid carrier substances suitable for consumption. Preferred compositions consist of the compound or compounds of the Formulae (I), (II), (III) or (IV) used according to the invention as well as the carrier substance or substances.

Advantageous carrier substances in these preferred (preferably spray-dried) compositions according to the invention are silicon dioxide (silicic acid, silica gel), carbohydrates and/or carbohydrate polymers (polysaccharides), cyclodextrins, starches, degraded starches (starch hydrolysates), chemically or physically modified starches, modified celluloses, gum Arabic, ghatti gum, tragacanth, karaya, carragheen, guar seed flour, carob seed flour, alginates, pectin, inulin or xanthan gum. Preferred starch hydrolysates are multidextrins and dextrins.

Preferred carrier substances are silicon dioxide, gum Arabic and maltodextrins, wherein maltodextrins with DE values in the range 5 to 20 are in turn preferred. In this connection it is unimportant which plant originally provided the starch for the production of the starch hydrolysates. Maize (corn)-based starches as well as starches obtained from tapioca, rice, wheat or potatoes are suitable and readily available. The carrier substances may at the same time also act as flow auxiliaries (anti-blocking agents), such as for example silicon dioxide.

The compositions according to the invention, which apart from the compound or compounds of the Formulae (I), (II), (III) or (IV) according to the invention also contain one or more solid carrier substances, can be produced for example by mechanical mixing processes, in which at the same time a comminution of the particles can also take place, or can be produced by means of spray drying. Preferred are compositions according to the invention which include solid carrier substances and are produced by means of spray drying; as regards spray drying reference is made to U.S. Pat. No. 3,159,585, U.S. Pat. No. 3,971,852, U.S. Pat. No. 4,532,145 or U.S. Pat. No. 5,124,162.

Preferred compositions according to the invention containing carrier substances and which have been produced by means of spray drying, have a mean particle size in the range from 30 to 300 μm and a residual moisture of less than or equal to 5 wt. %.

The weight ratio of the total mass of the compounds of the Formulae (I) (I), (II), (III) or (IV) used according to the invention to the solid carrier substances suitable for nutritional purposes is preferably in the range from 1:10 to 1:100000, more preferably in the range from 1:100 to 1:20000, particularly preferably in the range from 1:1000 to 1:5000, referred to the dry mass of the composition.

The sum of the constituents of (i) compounds of the Formulae (I), (II), (III) or (IV) to be used according to the invention, and (ii) the carrier substance or substances in the composition is preferably in the range from 70 to 100 wt. %, more preferably in the range from 85 to 100 wt. %.

The invention also relates to a (preferably spray-dried) composition, which apart from one or more compounds of the Formulae (I), (II), (III) or (IV) to be used according to the invention as well as (ii) solid carrier substances, includes in addition (iii) one or more aroma compositions, or consists of the aforementioned components.

Such an aroma composition within the context of the present invention includes at least one volatile aroma substance (however, this term is understood as not including compounds of the Formula (I)). The volatile aroma substance is in this connection preferably a sensorially active component with a vapour pressure of greater than or equal to 0.01 Pa at 25° C., preferably with a vapour pressure of greater than or equal to 0.025 Pa at 25° C. The majority of volatile aroma substances have a vapour pressure of greater than or equal to 1 Pa at 25° C., and these aroma substances are therefore regarded as preferred for use in compositions according to the invention.

Examples of aroma substances which can be a constituent of the aroma composition can be found for example in K. Bauer, D. Garbe and H. Surburg, Common Fragrance and Flavor Materials, 4th. Ed., Wiley-VCH, Weinheim 2001. The following for example may be mentioned: organic acids (saturated and unsaturated), such as for example butyric acid, acetic acid, methylbutyric acid, caproic acid; alcohols (saturated and unsaturated), such as for example ethanol, propylene glycol, octenol, cis-3-hexenol, benzyl alcohol; sulfides and disulfides, such as for example dimethyl sulfide, difurfuryl disulfide, methylthiopropanal; thiols such as for example methylfuranthiol; pyrazines and pyrrolines such as for example methylpyrazine, acetylpyrazine, 2-propionylpyrroline, 2-acetylpyrroline.

The aroma compositions can also be used in the form of reaction aromas (Maillard products) and/or extracts and/or essential oils of plants or plant parts and/or fractions thereof.

A further preferred composition according to the invention suitable for consumption, which includes one or more compounds of the Formulae (I), (II), (III) or (IV) used according to the invention, is a water-in-oil (W/O) emulsion. In addition to the compound or compounds of the Formulae (I), (II), (III) or (IV) used according to the invention, such an emulsion includes water, an oily phase, one or more W/O emulsifiers, optionally one or more antioxidants and optionally one or more substances for intensifying an antioxidative action.

Preferably such a composition (W/O emulsion) according to the invention contains
    0.01 to 0.1 wt. % of one or more compounds of the Formulae (I), (II), (III) or (IV) used according to the invention,
    5 to 30 wt. %, preferably 8 to 25 wt. % of water,
    50 to 90 wt. %, preferably 60 to 80 wt. % of an oily phase,
    0.1 to 5 wt. % of an edible W/O emulsifier, and also
    optionally one or more antioxidants and optionally one or more substances for intensifying an antioxidative action.

Such a W/O emulsion according to the invention particularly preferably consists of the aforementioned constituents in the aforementioned amounts.

The oily phase of such a W/O emulsion according to the invention contains (or consists of) preferably a fatty oil and/or an aroma composition. Preferred are oily phases containing or consisting of a fatty oil and an aroma composition.

Edible oils, in particular vegetable oils, are for example suitable as fatty oils. Suitable fatty oils are for example borage oil, thistle oil, groundnut oil, hazelnut oil, coconut oil, pumpkin seed oil, linseed oil, maize germ oil, macadamia nut oil, almond oil, olive oil, palm kernel oil, pecan nut oil, pistachio nut oil, rapeseed oil, rice seed oil, sesame oil, soya oil (soy bean oil), sunflower oil, walnut oil or wheat germ oil, or fractions obtainable therefrom. Liquid neutral esters based on medium chain length fatty acids and glycerol can also be used, such as for example miglyols (for example miglyol 810, miglyol 812). Sunflower oil, palm kernel oil and rapeseed oil are preferred. Furthermore, fractionated coconut oils which principally contain fatty acid residues with 6 to 8 C atoms are preferably used. These are characterized by their taste neutrality as well as by their good oxidation stability.

Preferably the edible W/O emulsifier is selected from the group consisting of lecithin (E 322), monoglycerides and diglycerides of edible fatty acids (E 471), acetic acid monoglycerides (E 472a), lactic acid monoglycerides (E 472b), citric acid monoglycerides (E 472c), tartaric acid monoglycerides (E 472d), diacetyltartaric acid monoglycerides (E 472e), and sorbitan monostearate (E 491).

Suitable antioxidants and substances which can intensify the antioxidative action are the naturally occurring tocopherols and their derivatives, tocotrienols, flavonoids, ascorbic acids and its salts, alpha-hydroxy acids (for example citric acid, lactic acid, malic acid, tartaric acid) and their Na, K and Ca salts, constituents isolated from plants, or extracts or fractions thereof, for example from tea, green tea, algae, grape seeds, wheat germs, rosemary, oregano, flavonoids, quercetin, phenolic benzylamines. Also suitable as antioxidants are propyl gallate, octyl gallate, dodecyl gallate, butylhydroxyanisole (BHA), butylhydroxytoluene (BHT), lecithins, monoglycerides and diglycerides of edible fatty acids esterified with citric acid, orthophosphates, and Na, K and Ca salts of monophosphoric acid and ascorbyl palmitate.

The W/O emulsions according to the invention are particularly suitable for application to foodstuffs surfaces, the foodstuffs preferably having a water content of at most 10 wt. %, preferably of at most 5 wt. %. In a preferred embodiment the W/O emulsion according to the invention has at the application temperature a sufficiently low viscosity so that it is possible to apply the W/O emulsion by means of spraying. Preferred foodstuffs on the surface of which a W/O emulsion according to the invention can be applied are for example crackers, chips/crisps (for example based on potatoes, maize, grain or bread), extruded nibbles/snack articles (e.g. flips) or pretzel-type articles (e.g. salted sticks or straws). W/O emulsions according to the invention are normally applied to the foodstuffs surfaces in an amount of 0.5 to 6 wt. %, referred to the total weight of the foodstuff.

As already mentioned, one aspect of the present invention relates to the use of a compound of the above Formulae (I), (II), (III) or (IV) (in particular a compound specified above as preferred) for the production, modification or intensification of an umami taste.

Preferably the compounds of the Formulae (I), (II), (III) or (IV) used according to the invention (in a flavor-active amount) or the compositions according to the invention are employed in (i) ready-to-serve or ready-to-eat preparations or (ii) semi-finished products serving for nutritional or consumption purposes, in particular in preparations with reduced sodium glutamate content or free from sodium glutamate serving for nutritional or consumption purposes.

The term "reduced sodium glutamate content" means that the preparation or semi-finished product according to the invention contains significantly less sodium glutamate than is contained in the conventional preparation or semi-finished product; the sodium glutamate content is in this connection 5 to <100 wt. %, preferably 10 to 50 wt. %, particularly preferably 20 to 50 wt. % below the sodium glutamate content of the conventional preparation. If a preparation of semi-finished product according to the invention contains, apart from one or more compounds of the Formulae (I), (II), (III) or (IV) used according to the invention, also sodium glutamate, then the weight ratio of the total amount of compounds of the Formulae (I), (II), (III) or (IV) to sodium glutamate is preferably in the range from 1:1 to 1:200.

According to the invention ready-to-serve or ready-to-eat preparations serving for nutritional or consumption purposes contain one or more compounds of the Formulae (I), (II), (III) or (IV) used according to the invention, preferably in an amount in the range from 0.01 ppm to 100 ppm, more preferably in the range from 0.1 ppm to 50 ppm, particularly preferably in the range from 0.1 ppm to 30 ppm, most preferably in the range from 1 ppm to 30 ppm, referred to the total weight of the ready-to-serve or ready-to-eat preparation.

Semi-finished products according to the invention serving for nutritional or consumption purposes contain one or more compounds of the Formulae (I), (II), (III) or (IV) to be used according to the invention, preferably in an amount in the range from 10 ppm to 800 ppm, more preferably in the range from 25 ppm to 750 ppm, particularly preferably in the range from 50 ppm to 700 ppm, referred to the total weight of the semi-finished product.

Particularly relevant are sodium glutamate-reduced preparations according to the invention which contain sodium glutamate, wherein the amount of sodium glutamate is not sufficient to be detected as a satisfactory umami taste in a comparison preparation that does not contain a mixture according to the invention but is of otherwise identical composition (normal sodium glutamate-reduced preparation), and the amount of the mixture according to the invention is sufficient to achieve a satisfactory umami taste impression.

Preparations in the context of the invention serving for nutritional or consumption purposes are in particular bakery items (e.g. bread, crackers/biscuits, cakes, other baked items), beverages (e.g. vegetable juices, vegetable juice preparations), instant drinks (e.g. instant vegetable drinks), meat products (e.g. ham, fresh sausage or raw sausage preparations), spicy or marinated fresh or pickled fish products (e.g. surimi), eggs or egg products (dried eggs, egg white, egg yellow), cereal products (e.g. pre-cooked ready-to-serve rice products, rice flour products, millet and sorghum products, raw or pre-cooked noodles and pasta products), dairy produce (e.g. fresh cheese, soft cheese, hard cheese, milk drinks, whey, butter, partially or wholly hydrolysed milk protein-containing products), products from soya protein or other soya bean fractions (e.g. soya milk and products prepared therefrom), soya lecithin-containing preparations, fermented products such as tofu or tempe, or products prepared therefrom, soya sauces), vegetable preparations (e.g ketchups, sauces, dried vegetables, deepfrozen vegetables, pre-cooked vegetables, vegetables pickled in vinegar, vegetable concentrates or pastes, boiled vegetables, potato preparations), nibble/snack articles (e.g. baked or fried potato crisps or potato dough products, bread dough products, extrudates based on maize, rice or groundnuts), products based on fats and oils or emulsions thereof (e.g. mayonnaise, remoulade, spreads, dressings, spice preparations), other ready-to-serve dishes and soups (e.g. dried soups, instant soups, pre-cooked soups), sauces (instant sauces, dried sauces, ready-to-serve sauces), spices, seasonings or spice/seasoning preparations (e.g. mustard preparations, horseradish preparations, marinades), spice mixtures as well as, in particular, seasonings, which are used for example in the snack sector.

Particularly preferred are (sodium glutamate-reduced) sodium glutamate-containing semi-finished products or preparations serving for nutritional or consumption purposes, e.g. bakery items (bread, crackers/biscuits, cakes, other bakery items), vegetable juice preparations, meat products (e.g. ham, fresh sausage or raw sausage preparations, spicy or marinated fresh or pickled meat products), eggs or egg products (dried eggs, egg white, egg yellow), cereal products (e.g. pre-cooked ready-to-serve rice products, raw or pre-cooked noodles and pasta products), dairy produce (e.g. fresh cheese, soft cheese, hard cheese, milk drinks, whey, butter, partially or wholly hydrolysed milk protein-containing products), products from soya protein or other soya bean fractions (e.g. soya milk and products prepared therefrom), soya lecithin-containing preparations, fermented products such as tofu or tempe or products prepared therefrom, soya sauces), fish sauces such as for example anchovy sauces, oyster sauces, vegetable preparations (e.g ketchups, sauces, dried vegetables, deepfrozen vegetables, pre-cooked vegetables, vegetables pickled in vinegar, boiled vegetables, potato preparations), nibbles/snack articles (e.g. baked or fried potato crisps or potato paste products, bread dough products, extracts based on maize or groundnuts), products based on fats and oils or emulsions thereof (e.g. mayonnaise, remoulades, dressings, spice preparations), ready-to-serve dishes, soups (e.g. dried soups, instant soups, pre-cooked soups), soup or bouillon cubes, sauces (instant sauces, dried sauces, ready-to-serve sauces), spices, relishes, condiments, spice mixtures as well as, in particular, seasonings, which are used for example in the snack sector.

The preparations in the context of the invention can also be in the form of capsules, tablets (non-coated as well as coated tablets, e.g. coatings resistant to gastric juices), pills, granules, pellets, solid mixtures, dispersions in liquid phases, as emulsions, as powders, as solutions, as pastes or as other preparations that can be swallowed or chewed, for example as dietary and nutritional supplements.

The semi-finished products according to the invention serve as a rule for the production of ready-to-serve or ready-to-eat preparations serving for nutritional or consumption purposes.

In particular semi-finished products according to the invention and serving for nutritional or consumption purposes can be used to intensify the umami taste of nutritional and food products with reduced sodium glutamate content, and can also be used directly as spices for the industrial or non-industrial preparation of nutritional and/or food products.

Semi-finished products according to the invention preferably contain a total amount of 10 ppm to 800 ppm, more preferably 25 ppm to 750 ppm and in particular 50 ppm to 700 ppm of compounds of the Formulae (I), (II), (III) or (IV) to be used according to the invention,
contain no sodium glutamate or an amount of 0.00001 wt. % to 10 wt. %, preferably 0.0001 wt. % to 5 wt. % and in particular 0.001 wt. % to 2 wt. % of sodium glutamate,
and optionally contain an amount of 0.0001 wt. % to 90 wt. %, preferably 0.001 wt. % to 30 wt. % of an aroma composition, in each case referred to the total weight of the semi-finished products.

The preparations or semi-finished products according to the invention are preferably produced by dissolving and mixing the compounds of the Formulae (I), (II), (III) or (IV) to be used according to the invention in mixtures of ethanol and optionally demineralized and/or purified water, following which the solutions are converted by a drying process, preferably a spray drying, vacuum freeze drying, reverse osmosis, vaporisation or other concentration process or a combination of the aforementioned processes, into an (at least almost) solid preparation. In this connection the drying can take place with the assistance of carrier substances (for example starch, starch derivatives, maltodextrin, silica gel, see above) or auxiliary substances (for example natural gums, stabilising agents). The drying is preferably carried out by means of spray drying or vacuum freeze drying.

Preferred preparations or semi-finished products according to the invention are spices, spice mixtures, condiments, soup cubes, instant soups, instant sauces, vegetarian ready-cooked dishes, meat-containing ready-cooked dishes, fish sauces such as for example anchovy sauces, oyster sauces, and soya sauces.

According to a further preferred embodiment, for the production of preparations or semi-finished products according to the invention compounds of the Formulae (I), (II), (III) or (IV) to be used according to the invention as well as optionally other constituents are first of all incorporated into emulsions, into liposomes (for example obtained from phosphatidyl choline), into microspheres, into nanospheres or also into capsules, granules or extrudates of a matrix suitable for foodstuffs and luxury foods (for example from starch, starch derivatives, cellulose or cellulose derivatives such as hydroxypropylcellulose, other polysaccharides such as alginate, natural fats, natural waxes such as beeswax or carnauba wax, or from proteins such as gelatins).

In a further preferred production process the compounds of the Formulae (I), (II), (III) or (IV) to be used according to the invention are complexed with one or more suitable complex-forming agents, for example with cyclodextrins or cyclodextrin-derivatives, preferably alpha-cyclodextrin or beta-cyclodextrin, and are employed in this complexed form.

Particularly preferred are preparations according to the invention in which the matrix is chosen so that the compounds of the Formulae (I), (II), (III) or (IV) to be used according to the invention are released in a delayed manner from the matrix, so that a long-lasting action is obtained. In this case for example natural fats, natural waxes (for example beeswax, carnauba wax), or also natural bulking substances (wheat fibres, apple fibres, oat fibres, orange fibres) can be used as matrix.

Further constituents (ingredients) of a ready-to-eat preparation or semi-finished product according to the invention serving for nutritional or consumption purposes can be conventional base substances, auxiliary substances and additives for nutritional or consumption purposes, for example water, mixtures of fresh or processed, vegetable or animal base substances or raw materials (for example raw, roasted, dried, fermented, smoked and/or cooked meat, bones, cartilage, fish, vegetables, herbs, nuts, vegetable juices or pastes or mixtures thereof), digestible or indigestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. suet, lard, palm oil, coconut butter, hardened vegetable oil), oils (for example sunflower oil, groundnut oil, maize seed oil, olive oil, fish oil, soya oil, sesame oil), fatty acids or their salts (e.g. potassium stearate), proteinaceous or non-proteinaceous amino acids and related compounds (for example γ-aminobutyric acid, taurine), peptides (for example glutathione), natural or processed proteins (for example gelatins), enzymes (for example peptidases), nucleic acids, nucleotides, taste corrigents for unpleasant taste impressions, further taste modulators for further, generally unpleasant taste impressions, other taste-modulating substances (for example inositol phosphate, nucleotides such as guanosine monophosphate, adenosine monophosphate or other substances such as sodium glutamate or 2-phen-oxypropionic acid), emulsifiiers (for example lecithins, diacyl glycerols, gum arabic), stabilizers (for example carrageen, alginate), preservatives (for example benzoic acid and its salts, sorbic acid and its salts), antioxidants (for example tocopherol, ascorbic acid), chelating agents (for example citric acid), organic or inorganic acidifying agents (for example acetic acid, phosphoric acid), additional bitter principles (for example quinine, caffeine, limonine, amarogentin, humolones, lupolones, catechols, tannins), substances preventing enzymatic browning (for example sulfite, ascorbic acid), essential oils, plant extracts, natural or synthetic dyes or coloured pigments (for example carotinoids, flavonoids, anthocyans, chlorophyll and derivatives thereof), spices, trigeminally-active substances or plant extracts containing such trigeminally-active substances, synthetic, natural or natural-identical aroma substances or fragrances, as well as olfactory corrigents.

Preferably compositions, preparations or semi-finished products according to the invention contain an aroma composition in order to round off and refine the taste and/or the smell. A composition according to the invention which contains as further constituents a solid carrier substance and an aroma composition, has already been described in more detail above. Suitable aroma compositions contain for example synthetic, natural or natural-identical aroma substances, fragrances and flavor substances, reaction aromas, smoke aromas or other aroma-imparting preparations (for example protein (partial) hydrolysates, grill aromas, plant extracts, spices, spice preparations, vegetables and/or vegetable preparations) as well as suitable auxiliary substances and carrier substances. In particular, suitable in this case are the aroma compositions not according to the invention or their constituents which produce a roasted, fish/meat-like (in particular chicken, fish, seafood, beef, pork, lamb, mutton, goat), vegetable-like (in particular tomato, onion, garlic, celery, leek, mushroom, aubergine, seaweed), spicy (in particular black and white pepper, chilli, paprika, cardamom, nutmeg, all-spice, mustard and mustard products), roasted, yeast-like, boiled, fatty/oily, salty and/or sharp aroma impression and can thus intensify the spicy impression. As a rule the aroma compositions contain more than one of the aforementioned ingredients.

In a further modification of the present invention the compounds of the Formulae (I), (II), (III) or (IV) to be used according to the invention are employed in the compositions, preparations and semi-finished products according to the invention in combination with at least one (further, not per se according to the invention) substance in order to mask or reduce an unpleasant (bitter, metallic, chalky, acidic, astringent) taste impression or to intensify or produce a pleasant taste impression (sweet, salty, umami). In this way an intensification of the taste, in particular the umami taste, can be achieved. These further substances can be chosen from the following list, without however restricting the invention: monosodium glutamate, glutamic acid, nucleotides (for example adenosine-5'-monophosphate, cytidine-5'-monophosphate, inosine-5'-monophosphate, guanosine-5'-monophosphate) or their pharmaceutically acceptable salts, lactisols, hydroxyflavanones (for example eriodictyol, homoeriodictyol or their sodium salts), in particular according to EP 1 258 200, hydroxybenzoic acid amides (for example 2,4-dihydroxybenzoic acid vanillylamide, 4-hydroxybenzoic acid vanillylamide), mixtures of whey proteins with lecithins, yeast extracts, plant hydrolysates, powdered vegetables (for example onion powder, tomato powder), plant extracts (for example from lovage or from mushrooms such as shiitake), seaweed and mineral salt mixtures.

Modulating aroma substances and/or flavor substances are preferably selected from the group consisting of adenosine-5'-monophosphate, cytidine-5'-monophosphate, inosine-5'-monophosphate, and their pharmaceutically acceptable salts; lactisols; 2,4-dihydroxybenzoic acid; 3-hydroxybenzoic acid; sodium salts, preferably sodium chloride, sodium lactate, sodium citrate, sodium acetate, sodium gluconate; hydroxyflavonones, such as for example eriodictyol, homoeriodictyol and their sodium salts; hydroxybenzoic acid amides, such as for example 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxy-benzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide monosodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl) ethyl]amide; 4-hydroxybenzoic acid vanillylamide (in particular as described in WO 2006/024587, which as regards the corresponding compounds disclosed therein is on course to be referred to as a constituent part of the present application); hydroxydeoxybenzoins, such as for example 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone) (in particular those as described in WO 2006/106023, which as regards the corresponding compounds disclosed therein is on course to be referred to as a constituent part of the present application); hydroxyphenylalkanediones, such as for example ginger dione-[2], gingerdione-[3], gingerdione-[4], dehydrogingerdione-[2], dehydrogingerdione-[3], dehydrogingerdione-[4]) (in particular those as described in WO 2007/003527, which as regards the corresponding compounds disclosed therein is on course to be referred to as a constituent part of the present application); diacetyl trimers (in particular those as described in WO 2006/058893, which as regards the corresponding compounds disclosed therein is on course to be referred to as a constituent part of the present application); γ-aminobutyric acids (in particular those as described in WO 2005/096841, which as regards the corresponding compounds disclosed therein is on course to be referred to as a constituent part of the present application); and divanillins (in particular divanillin as described in WO 2004/078302, which as regards the corresponding compounds disclosed therein is on course to be referred to as a constituent part of the present application). It is also possible to include saliva-inducing/mouth-watering substances, preferably pellitorin, more preferably trans-pellitorin.

From the preceding text it follows that a further aspect of the present invention is also a process for generating, modifying or intensifying a flavor, in particular an umami flavor, in (i) a ready-for-use or ready-to-eat preparation or (ii) semi-finished product serving for nutritional or consumption purposes. Such a process according to the invention includes the following step:

Mixing a taste-active amount of one or more compounds of the Formulae (I), (II), (III) or (IV) or a composition according to the invention with one or more further constituents of the (i) ready-to-eat preparation or of the (ii) semi-finished product, or applying a taste-active amount of one or more compounds of the Formulae (I), (II), (III) or (IV) or of a composition according to the invention to one or more further constituents of the (i) ready-to-eat preparation or of the (ii) semi-finished product, or embedding a taste-active amount of one or more compounds of the Formulae (I), (II), (III) or (IV) or of a composition according to the invention in a shell or matrix material.

A further aspect of the present invention relates to new compounds of the Formulae (I), (II), (III) and (IV). In particular, the compounds already known from the document US 2004/0209859 A1, in particular the individual compounds listed hereinbefore, insofar as they fall under Formula (I), are not the subject-matter of the present invention, although their use is (see in this connection the accompanying patent claims). Preferably the compounds mentioned in the description, in particular in paragraphs [0059] to [0120], and the compounds mentioned in the examples of US 2004/0209859 A1, in particular in Examples 38 and 49, are not the subject-matter of the present invention. Preferably also the products of the syntheses described in the examples, in particular in Examples 38 and 49, are not the subject-matter of the present invention. It is provisionally preferred that all individual compounds mentioned hereinbefore in the disclosures of document US 2004/0209859 A1 are not the subject-matter of the present invention, as well as those in which it is not clear whether they have actually been disclosed.

A further aspect of the present invention relates to a process for the production of a compound of the Formulae (IVa), (IVc), (E), (B), (P) or (H) comprising the following steps:

reacting a compound of the Formula (V),

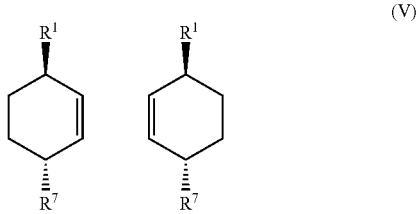

with a compound capable of forming a carbene, preferably in a rhodium-catalyzed or copper-catalyzed reaction, wherein a compound of the Formula (VI) is formed (and in addition normally further diastereomers)

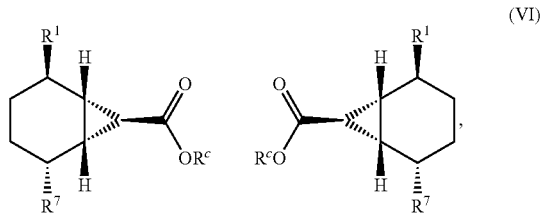

where R1 denotes alkyl,
saponification of the compound of the Formula (VI) to form a compound of the Formula (VII)

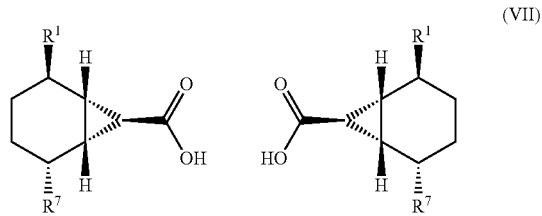

conversion of the compound of the Formula (VII) to the corresponding acid chloride (by reaction with a compound suitable for the production of acid chlorides) and subsequent reaction of the acid chloride with a compound of the formula NH2-Rb,
wherein R1, R7 and Rb have the meanings given above.

Compounds of the Formula (V) can be prepared in a similar manner to that described in Roczniki Chemii Ann. Soc. Chim. Polonorum 1976, 50, 1901-1908.

A compound capable of forming a carbine, with which a compound of the Formula (V) is reacted, is preferably an alkyl diazoacetate. Particularly preferred in this connection is ethyl diazoacetate (diazoacetic acid ester). A compound of the Formula (V) reacts with ethyl diazoacetate to form a compound of the Formula (VI), in which Rc denotes ethyl.

Preferred compounds suitable for the preparation of acid chlorides are oxalyl chloride or thionyl chloride.

Preferably, in a preparation process according to the invention R1 denotes methyl, R7 denotes isopropyl and Rb denotes ethyl, cyclopropyl, cyclobutyl, cyclopentyl or cyclohexyl.

The invention will now be described in more detail hereinafter with the aid of examples. Further aspects of the present invention are disclosed in the accompanying claims.

DESCRIPTION OF THE FIGURES

The test panel evaluated the strength of the specified flavors in each case by awarding points on a scale from 0 (no corresponding taste) to 6 (very pronounced corresponding taste). The mean values of the respective scores are shown.

The taste of a 0.5% American beef extract as base (continuous, pale line) was compared on the basis of an evaluation by a panel of trained testers with the taste firstly of such a base to which 5 ppm of (1R,2S,5R,6S,7R)-2-isopropyl-5-methyl-bicyclo[4.1.0]heptane-7-carboxylic acid ethylamide had been added (continuous, dark line), and secondly of such a base to which 0.05 wt. % of MSG had been added (dotted line).

Figure 1:
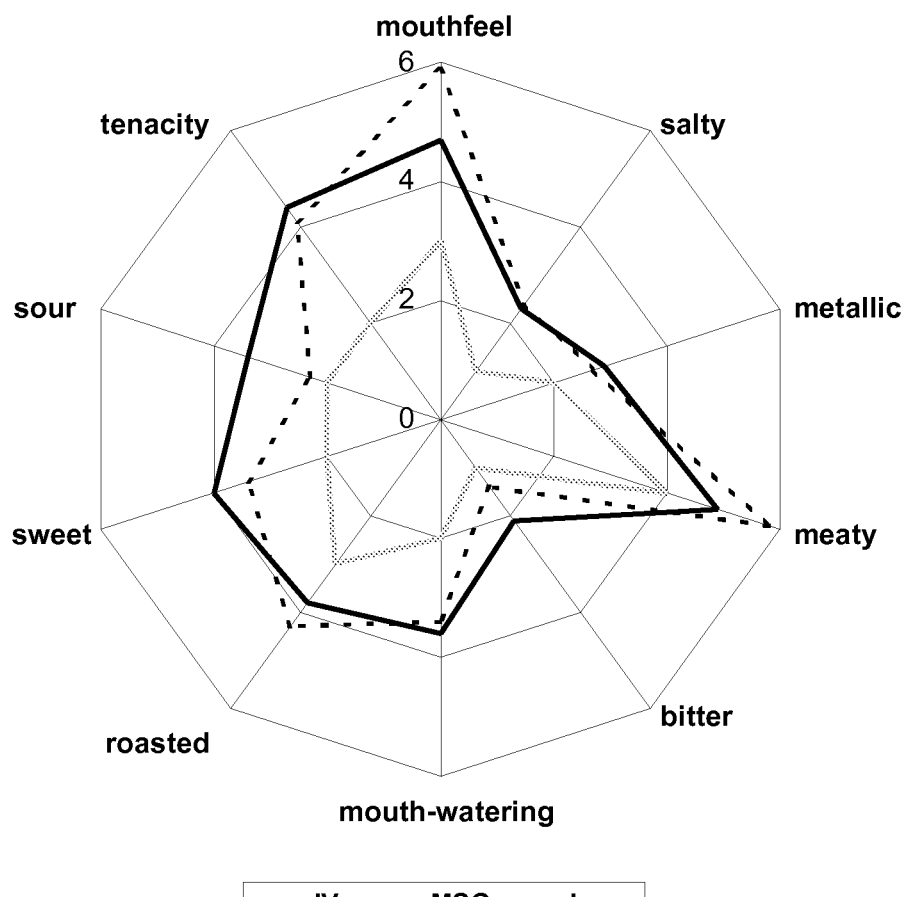
FIG. 1: Taste comparison of (1R,2S,5R,6S,7R)-2-isopropyl-5-methyl-bicyclo[4.1.0]heptane-7-carboxylic acid ethylamide with sodium glutamate.
Figure 2:
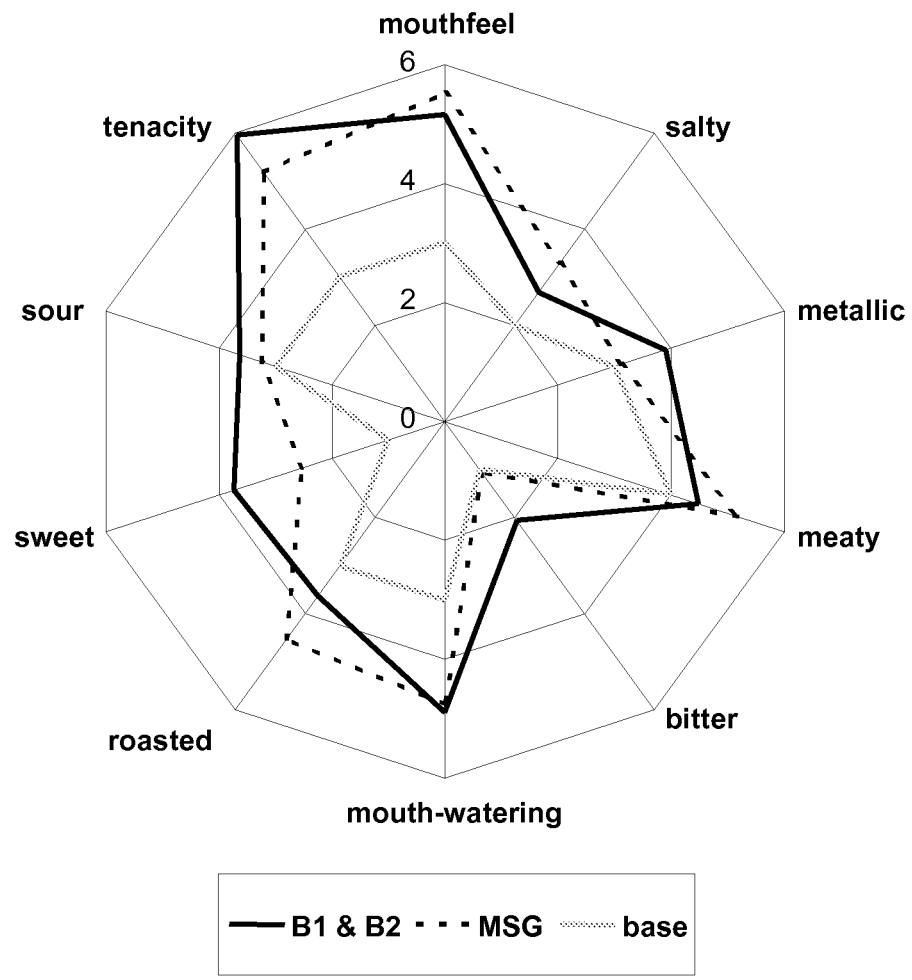

FIG. 2: Taste comparison of a mixture of (1S,2S,5R,6R,7S)-2-isopropyl-5-methyl-bicyclo[4.1.0]heptane-7-carboxylic acid cyclobutylamide (B1) and (1R,2S,5R,6S,7R)-2-isopropyl-5-methyl-bicyclo[4.1.0]heptane-7-carboxylic acid cyclobutylamide (B2) with sodium glutamate.

The taste of a 0.5% American beef extract as base (continuous, pale line) was compared on the basis of an evaluation by a panel of trained testers to the taste firstly of such a base to which 2 ppm of a mixture of 1S,2S,5R,6R,7S)-2-isopropyl-5-methyl-bicyclo[4.1.0]heptane-7-carboxylic acid cyclobutylamide (B1) and (1R,2S,5R,6S,7R)-2-isopropyl-5-methyl-bicyclo[4.1.0]heptane-7-carboxylic acid cyclobutylamide (B2) had been added (continuous, dark line), and secondly of such a base to which 0.05 wt. % of MSG had been added (dotted line).

Figure 3:
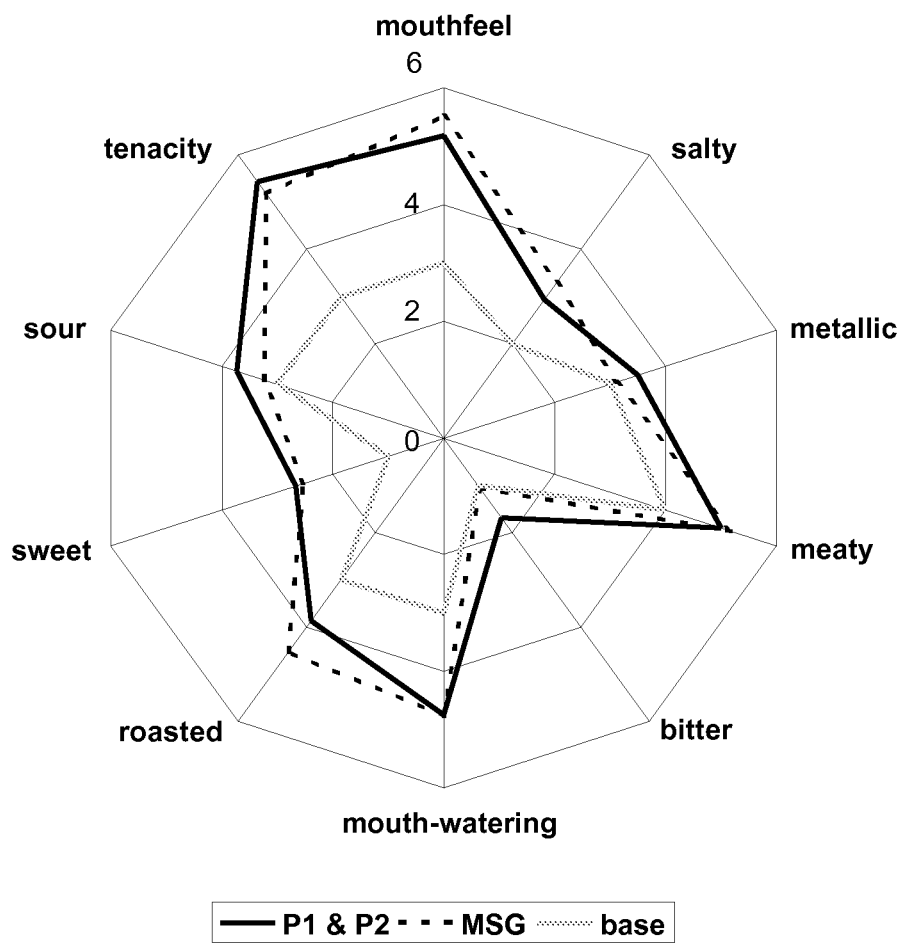

FIG. 3: Taste comparison of a mixture of (1S,2S,5R,6R,7S)-2-isopropyl-5-methyl-bicyclo[4.1.0]heptane-7-carboxylic acid cyclopentylamide (P1) and (1R,2S,5R,6S,7R)-2-isopropyl-5-methyl-bicyclo[4.1.0]heptane-7-carboxylic acid-cyclopentylamide (P2) with sodium glutamate.

The taste of a 0.5 wt. % American beef extract as base (continuous, pale line) was compared on the basis of an evaluation by a panel of trained testers with the taste firstly of such a base to which 0.5 ppm of a mixture of (1S,2S,5R,6R,7S)-2-Isopropyl-5-methyl-bicyclo[4.1.0]heptane-7-carboxylic acid cyclopentylamide (P1) and (1R,2S,5R,6S,7R)-2-isopropyl-5-methyl-bicyclo[4.1.0]heptane-7-carboxylic acid cyclopentylamide (P2) had been added (continuous, dark line), and secondly of such a base to which 0.05 wt. % of MSG had been added (dotted line).

EXAMPLES

Synthesis Example 1

(2S,5R)-2-isopropyl-5-methyl-bicyclo[4.1.0]heptane-7-carboxylic acid ethylamide

Synthesis Example 1a (2S,5R)-2-isopropyl-5-methyl-bicyclo[4.1.0]heptane-7-carboxylic acid ethyl ester 98.4 g of a technical mixture of menthenes (60% (+)-p-menth-2-ene, 16.4% p-3-menthene) and 120 mg of rhodium (II) acetate dimer dihydrate are placed in a 500 ml three-necked flask equipped with magnetic stirrer, contact thermometer and high-efficiency condenser. 40.8 g of a 35% solution of ethyl diazoacetate (diazoacetic acid ethylester) in dichloromethane are added at 40° C. over 4 hours while stirring. The reaction mixture is stirred for a further 2 hours at 40° C., and the crude product is washed twice with 75 ml of water, dried over sodium sulfate, and excess menthene is distilled off under vacuum.

The crude product is purified by chromatography on 90 g of silica gel (diethyl-ether/hexane=1/20). 1.4 g of a product fraction containing 92% of 2-isopropyl-5-methyl-bicyclo[4.1.0]heptane-7-carboxylic acid ethyl ester and 1.9 g of a second fraction containing 66% of the desired ester are obtained.

Synthesis Example 1b (2S,5R)-2-isopropyl-5-methyl-bicyclo[4.1.0]heptane-7-carboxylic acid 1.9 g of 2-isopropyl-5-methyl-bicyclo[4.1.0]heptane-7-carboxylic acid ethyl ester (66%) from synthesis example 1a are boiled under reflux for 3 hours with 20 ml of 10% sodium hydroxide solution. 25 ml of 10% hydrochloric acid are added and the mixture is extracted twice with 50 ml of diethyl ether. The organic phases are dried with sodium sulfate and the solvent is distilled off under vacuum. 1.37 g of a crude product containing 69% of the 2-isopropyl-5-methyl-bicyclo[4.1.0]heptane-7-carboxylic acid isomers are obtained.

Synthesis Example 1c (2S,5R)-2-Isopropyl-5-methyl-bicyclo[4.1.0]heptane-7-carboxylic acid ethylamide 1.37 g of 2-isopropyl-5-methyl-bicyclo[4.1.0]heptane-7-carboxylic acid from Synthesis Example 1b are dissolved in 30 ml of diethyl ether and 1.07 g of oxalyl chloride are added at room temperature while stirring. The reaction mixture is stirred for 2 hours at room temperature and the solvent is removed under vacuum.

The crude acid chloride is dissolved in dichloromethane. 5.7 ml of ethylamine solution (70% in water) are added dropwise while stirring. The reaction mixture is stirred for 16 hours at room temperature, washed twice with 10 ml of water, dried over sodium sulfate and the solvent is distilled off under vacuum.

The crude product is purified by chromatography on 60 g of silica gel (diethyl ether/hexane=1/4). The following fractions are obtained: A) 0.63 g of 2-isopropyl-5-methyl-bicyclo[4.1.0]heptane-7-carboxylic acid ethylamide with a purity of >98% (ratio of the (1R,2S,5R,6S,7R) isomer to the (1S,2S,5R,6R,7S) isomer ca. 1:1), B) 250 mg with the following composition: 2-isopropyl-5-methyl-bicyclo[4.1.0]heptane-7-carboxylic acid ethylamide isomer (1S,2S,5R,6R,7S) 34.3%, isomer (1R,2S,5R,6S,7R) 53.5%, two isomers of 1-isopropyl-4-methyl-bicyclo[4.1.0]heptane-7-carboxylic acid ethylamide 4.4% and 3.1%, and C) 230 mg with 80% of N-ethyl-2-(4-isopropyl-1-methyl-cyclohex-2-enyl)-acetamide.

The fraction B is purified further by preparative HPLC.
Preparative HPLC:
Column: Grom sapphire 110 Si, 5 μm 125+150×20 mm
Eluent: Heptane/MTBE (65/35)
Mode: isocratic
Flow rate: 15 ml/min
Pressure: 31 bar
Temperature: Room temperature
Detection: 265 nm
Isolates from the preparative HPLC:
Fraction 1: 5 mg 1-isopropyl-4-methyl-bicyclo[4.1.0]heptane-7-carboxylic acid ethylamide Analysis Data:
MS (EI): m/z=29 (13%), 41 (12), 55 (12), 72 (25), 81 (12), 87 (100), 88 (28), 95 (15), 109 (12), 136 (12), 223 (7, M$^+$).
Fraction 2: 34 mg (1R,2S,5R,6S,7R)-2-isopropyl-5-methyl-bicyclo[4.1.0]heptane-7-carboxylic acid ethylamide (Compound of the Formula (IVc))

Analysis Data:
$^1$H-NMR (400 MHz, CDCl$_3$): δ=0.56 (mc, 1H), 0.73-0.84 (m, 1H), 0.91 (d, J=6.7 Hz, 3H), 0.94 (d, J=6.6 Hz, 3H), 1.01 (t, J=4.5 Hz, 1H), 1.09 (d, J=6.8 Hz, 3H), 1.14 (t, J=7.2 Hz, 3H), 1.31 (ddd, J=1.8, 4.2, 9.2 Hz, 1H), 1.31-1.41 (m, 1H), 1.44-1.56 (m, 3H), 1.57-1.65 (m, 2H), 3.29 (q, J=7.2 Hz, 1H), 3.31 (q, J=7.2 Hz, 1 5.46 (sb, 1H).
$^{13}$C-NMR (100 MHz, CDCl$_3$): δ=15.1 (CH3), 20.5 (CH3), 20.7 (CH3), 23.4 (CH$_3$), 24.8 (CH2), 25.6 (CH), 26.0 (CH), 27.4 (CH), 30.4 (CH), 32.7 (CH2), 33.6 (CH), 34.5 (CH2), 39.9 (CH) 173.4 (C=O).
MS (EI): m/z=29 (32%), 67 (32), 72 (38), 87 (99), 88 (40), 95 (29), 109 (55), 138 (62), 180 (100), 223 (10, NC).
Fraction δ: 15 mg (1S,2S,5R,6R,7S)-2-isopropyl-5-methyl-bicyclo[4.1.0]heptane-7-carboxylic acid ethylamide Analysis Data:
$^1$H-NMR (400 MHz, CDCl$_3$): δ=0.53 (mc, 1H), 0.91 (d, J=6.8 Hz, 3H), 0.93 (d, J=6.8 Hz, 3H), 0.97 (d, J=6.6 Hz, 3H), 0.98 (mc, 1H), 1.14 (t, J=7.3 Hz, 3H), 1.20-1.32 (m, 2H), 1.35-1.53 (m, 3H), 1.54-1.71 (m, 2H), 1.84-1.94 (m, 1H), 3.29 (mc, 2H), 5.63 (sb, 1H).
$^{13}$C-NMR (100 MHz, CDCl$_3$): δ=14.9 (CH3), 19.2 (CH3), 19.9 (CH3), 21.4 (CH$_3$), 25.2 (CH), 25.3 (CH), 26.1 (CH2), 28.2 (CH), 28.7 (CH), 28.7 (CH2), 33.2 (CH), 34.4 (CH2), 41.8 (CH), 173.6 (C=O).
MS (EI): m/z=29 (26%), 55 (26), 72 (28), 81 (37), 87 (70), 95 (29), 109 (32), 138 (70), 180 (100), 223 (17, M$^+$).

Synthesis Examples 2-6

Synthesis of further substituted bicyclo[4.1.0]heptane-7-carboxylic acid amides

General Synthesis Procedure

Step a: Cyclopropanecarboxylic Acid Ethyl Ester by Addition of Ethyl Diazoacetate to Alkenes 0.15 mole of alkene and 0.45 mmol of rhodium(II) acetate (dimer, dihydrate) are added to 200 ml of dichloromethane. 0.15 mole of ethyl diazoacetate is added at 40° C. over a period of 6 hours while stirring. The reaction mixture is stirred for a further 2 hours, washed twice with 100 ml of water, dried over sodium sulfate, and the solvent is distilled off under vacuum.

The residue is filtered over 25 g of silica gel (diethyl ether/pentane=1/5). After removing the solvent the crude product is used for the saponification corresponding to the general procedure described in Synthesis Example 2b.

Step b: Cyclopropanecarboxylic Acid by Saponification of the Cyclopropanecarboxylic Acid Ethyl Ester 100 mmol of crude cyclopropanecarboxylic acid ester from Synthesis Example 2a are boiled under reflux in 100 ml of sodium hydroxide solution (10%) and 30 ml of ethanol for 3 hours. The reaction mixture is diluted with 100 ml of water and extracted twice, each time with 100 ml of diethyl ether.

120 ml of hydrochloric acid (10%) is added to the aqueous phase, which is extracted three times with in each case 100 ml of diethyl ether. The organic phase is dried with sodium sulfate and the solvent is distilled off under vacuum.

The crude material is used for the preparation of the acid chloride and the subsequent aminolysis to the ethylamide corresponding to the general procedure in Synthesis Example 2c.

Step c: Preparation of the Acid Chloride and Subsequent Aminolysis to the Alkylamide 50 mmol of crude cyclopropanecarboxylic acid from Synthesis Example 2b are dissolved in 100 ml of diethyl ether and 300 μl of DMF are added. 60 mmol of oxalyl chloride are added dropwise at 25° C. over a period of 30 minutes while stirring. The reaction mixture is stirred for 16 hours at room temperature.

200 mmol of alkylamine (70% in water) are added at 20° C. The reaction mixture is stirred for 4 hours at room temperature, diluted with 100 ml of diethyl ether, washed with respectively 50 ml of water, hydrochloric acid (10%), saturated sodium hydrogen carbonate solution and saturated sodium chloride solution, dried over sodium sulfate, and the solvent is removed under vacuum.

The crude product is purified by chromatography on silica gel (diethyl ether/pentane=½).

With purities<95% (according to GC), the product is purified further by preparative HPLC:
Column: Chromsil Sapphire 5 μm 125×20 mm
Eluent: 65% MeOH/35% water
Mode: isocratic
Flow rate: 80 ml/min
Pressure: 135 bar
Temperature: RT
Detection: 270 nm/R1

Synthesis Example 2

Tricyclo[3.2.1.0$^{2,4}$]octane-3-carboxylic acid N-ethylamide

The aforementioned substance was prepared according to the general synthesis procedure, norbornene being used as alkene.

Analysis Data:
$^1$H-NMR (400 MHz, CDCl$_3$): δ=0.68 (dquint, J=~1, 10.8 Hz, 1H), 0.88 (dquint, J=2.1, 10.8 Hz, 1H), 1.12 (t, J=7.3 Hz, 3H), 1.23 (t, J=2.5 Hz, 1H), 1.30-1.36 (m, 4H), 1.38-1.48 (m, 2H), 2.33 (s, 2H), 3.27 (dq, J=5.6, 7.3 Hz, 1.8H), 3.36 (dq, J=6.1, 7.3 Hz, 0.2H), 5.53 (sb, 1H).
$^{13}$C-NMR (100 MHz, CDCl3): δ=15.0 (CH3), 18.4 (CH), 24.6 (CH), 28.7 (CH2), 28.9 (CH2), 34.4 (CH2), 35.8 (CH), 172.9 (C=O).
MS (EI): m/z=29 (42%), 44 (33), 55 (30%), 72 (45), 79 (69), 87 (55), 91 (32), 124 (47), 150 (40), 179 (100, M$^+$).

Synthesis Example 3

Bicyclo[4.1.0]heptane-7-carboxylic acid N-ethylamide

The aforementioned substance was prepared according to the general synthesis procedure, cyclohexene being used as alkene.

Analysis Data:
$^1$H-NMR (400 MHz, CDCl$_3$): δ=1.07 (t, J=4.3 Hz, 1H), 1.14 (t, J=7.3 Hz, 3H), 1.12-1.35 (m, 4H), 1.54 (mc, 2H), 1.60-1.68 (m, 2H), 1.86-2.00 (m, 2H), 3.29 (dq, J=5.6, 7.3 Hz, 1.86), 3.36 (dq, J=6, 7.3 Hz, 0.14H), 5.61 (sb, 1H).
$^{13}$C-NMR (100 MHz, CDCl3): δ=15.0 (CH3), 20.4 (CH), 21.2 (CH2), 22.9 (CH2), 28.0 (CH), 34.5 (CH2), 173.5 (C=O).
MS (EI): m/z=29 (23%), 55 (38), 67 (26), 72 (20), 81 (22), 87 (20), 95 (27), 96 (20), 124 (100), 167 (59, M$^+$).

Synthesis Example 4

2-isopropyl-bicyclo[4.1.0]heptane-7-carboxylic acid ethylamide

The aforementioned substance was prepared according to the general synthesis procedure, 1-isopropylcyclohex-2-ene being used as alkene.

Analysis Data:
MS (EI): m/z=29 (22%), 41 (26), 55 (20), 67 (22), 72 (43), 81 (30), 87 (95), 95 (43), 124 (27), 166 (100), 209 (12, M$^+$).

Synthesis Example 5

2,4-dimethyl-bicyclo[4.1.0]heptane-7-carboxylic acid ethylamide

The aforementioned substance was prepared according to the general synthesis procedure, 1,3-dimethylcyclohex-4-ene being used as alkene.

Analysis Data:
$^1$H-NMR (400 MHz, C$_6$D$_6$): δ=0.36 (q, J=12.1 Hz, 1H), 0.77 (d, J=4.3 Hz, 1H), 0.79 (d, J=6.4 Hz, 3H), 0.84 (t, J=7.2 Hz, 3H), 0.91-0.98 (m, 1H), 1.00 (d, J=6.9 Hz, 3H), 1.10 (ddd, J=13.3, 11.9, 5.0 Hz, 1H), 1.25 (ddd, J=12.7, 5.2, 1.9 Hz, 1H), 1.48-1.58 (m, 2H), 1.78 (m$_c$, 1H), 1.86 (m$_c$, 1H), 3.13 (m$_c$, 1H), 4.90 (s$_b$, 1H).
$^{13}$C-NMR (100 MHz, CDCl3): δ=15.3 (CH$_3$), 22.7 (CH3), 23.1 (CH), 23.7 (CH3), 26.5 (CH), 27.1 (CH), 28.3 (CH), 31.6 (CH), 31.9 (CH2), 34.5 (CH2), 41.5 (CH2), 173.5 (C=O).
MS (EI): m/z=29 (28%), 55 (37), 67 (24), 72 (40), 81 (40), 87 (100), 88 (31), 124 (48), 138 (46), 195 (31, M$^+$).

Synthesis Example 6

Cyclopropanecarboxylic acid N-ethylamide (Not According to the Invention)

7.32 g of cyclopropanecarboxylic acid chloride (Aldrich, 70 mmol) are added to 100 ml of dichloromethane and 22.3 ml of ethylamine (70% solution in water) are slowly added while stirring. The reaction mixture is stirred for 14 hours at room temperature, diluted with 150 ml of diethyl ether, the organic phase is washed twice with 50 ml of water and 50 ml of saturated sodium chloride solution, dried over sodium sulfate, and the solvent is distilled off under reduced pressure. 5.2 g of cyclopropanecarboxylic acid N-ethylamide are obtained.

Analysis Data:
$^1$H-NMR (400 MHz, CDCl$_3$): δ=0.69-0.74 (m, 2H), 0.93-0.97 (m, 2H), 1.15 (t, J=7.3 Hz, 3H), 1.34 (mc, 1H), 3.31 (dq, J=5.6, 7.3 Hz, 2H), 5.86 (sb, 1H).
$^{13}$C-NMR (100 MHz, CDCl3): δ=6.9 (CH2), 14.7 (CH), 15.0 (CH3), 34.5 (CH2), 173.5 (C=O).

MS (EI): m/z=27 (11%), 29 (24), 39 (24), 41 (51), 44 (27), 55 (11), 69 (100), 72 (10), 51 (98), 112 (43, M–1⁺).

Synthesis Example 7

(1R,2S,5R,6S,7R)-2-isopropyl-5-methyl-bicyclo[4.1.0]heptane-7-carboxylic acid cyclobutylamide/
(1S,2S,5R,6R,7S)-2-isopropyl-5-methyl-bicyclo[4.1.0]heptane-7-carboxylic acid cyclobutylamide The aforementioned substance was prepared according to the general synthesis procedure, using (3S,6R)-3-isopropyl-6-methylcyclohexene as alkene and cyclobutylamine as amine. After crystallization an approx. 1:1 mixture of the two diastereomers was obtained.

(1S,2S,5R,6R,7S)-2-isopropyl-5-methyl-bicyclo[4.1.0]heptane-7-carboxylic acid cyclobutylamide
(Major Diastereomer)

MS (EI): m/z=41 (41), 43 (66), 55 (73), 69 (36), 81 (56), 93 (76), 95 (100), 135 (63), 179 (95), 221 (91), 249 (0.3, M⁺).

(1R,2S,5R,6S,7R)-2-isopropyl-5-methyl-bicyclo[4.1.0]heptane-7-carboxylic acid cyclobutylamide
(Minor Diastereomer)

MS (EI): m/z=43 (55), 55 (62), 81 (50), 93 (79), 95 (100), 135 (62), 136 (47), 178 (47), 179 (46), 221 (76), 249 (0.7, M⁺).

Synthesis Example 8

(1R,2S,5R,6S,7R)-2-isopropyl-5-methyl-bicyclo[4.1.0]heptane-7-carboxylic acid cyclopentylamide/
(1S,2S,5R,6R,7S)-2-isopropyl-5-methyl-bicyclo[4.1.0]heptane-7-carboxylic acid cyclopentylamide The aforementioned substance was prepared according to the general synthesis procedure, (3S,6R)-3-isopropyl-6-methyl-cyclohexene being used as alkene and cyclopentylamine being used as amine. After crystallization an approx. 2:3 mixture of the two diastereomers was obtained.

(1S,2S,5R,6R,7S)-2-isopropyl-5-methyl-bicyclo[4.1.0]heptane-7-carboxylic acid cyclopentylamide
(Major Diastereomer)

MS (EI): m/z=41 (43), 55 (30), 60 (36), 69 (45), 81 (28), 95 (36), 127 (49), 178 (53), 220 (100), 263 (31, M⁺).

(1R,2S,5R,6S,7R)-2-isopropyl-5-methyl-bicyclo[4.1.0]heptane-7-carboxylic acid cyclopentylamide
(Minor Diastereomer)

MS (EI): m/z=41 (48), 55 (30), 60 (51), 67 (30), 69 (59), 95 (34), 109 (44), 127 (79), 178 (46), 220 (100), 263 (29, M⁺).

Synthesis Example 9

(1R,2S,5R,6S,7R)-2-isopropyl-5-methyl-bicyclo[4.1.0]heptane-7-carboxylic acid cyclohexylamide/
(1S,2S,5R,6R,7S)-2-isopropyl-5-methyl-bicyclo[4.1.0]heptane-7-carboxylic acid cyclohexylamide The aforementioned substance was prepared according to the general synthesis procedure, using (3S,6R)-3-isopropyl-6-methylcyclohexene as alkene and cyclohexylamine as amine. After crystallization an approx. 2:3 mixture of the two diastereomers was obtained.

(1S,2S,5R,6R,7S)-2-isopropyl-5-methyl-bicyclo[4.1.0]heptane-7-carboxylic acid cyclohexylamide
(Major Diastereomer)

MS (EI): m/z=41 (31), 55 (51), 60 (33), 81 (30), 83 (29), 95 (33), 109 (27), 141 (38), 192 (45), 234 (100), 277 (20, M⁺).

(1R,2S,5R,6S,7R)-2-isopropyl-5-methyl-bicyclo[4.1.0]heptane-7-carboxylic acid cyclohexylamide
(Minor Diastereomer)

MS (EI): m/z=41 (36), 55 (59), 60 (52), 67 (29), 83 (38), 95 (35), 109 (40), 141 (73), 192 (40), 234 (100), 277 (15, M⁺).

Synthesis Example 10

(1R,2S,5R,6S,7R)-2-isopropyl-5-methyl-bicyclo[4.1.0]heptane-7-carboxylic acid isopropylamide/
(1S,2S,5R,6R,7S)-2-isopropyl-5-methyl-bicyclo[4.1.0]heptane-7-carboxylic acid isopropylamide The aforementioned substance was prepared according to the general synthesis procedure, using (3S,6R)-3-isopropyl-6-methyl-cyclohexene as alkene and isopropylamine as amine. After crystallization an approx. 2:3 mixture of the two diastereomers was obtained.

(1S,2S,5R,6R,7S)-2-isopropyl-5-methyl-bicyclo[4.1.0]heptane-7-carboxylic acid isopropylamide
(Major Diastereomer)

MS (EI): m/z=41 (34), 43 (60), 55 (25), 81 (31), 95 (30), 101 (60), 109 (30), 152 (61), 194 (100), 237 (31, M⁺).

(1R,2S,5R,6S,7R)-2-isopropyl-5-methyl-bicyclo[4.1.0]heptane-7-carboxylic acid isopropylamide
(Minor Diastereomer)

MS (EI): m/z=41 (37), 43 (81), 55 (28), 67 (28), 86 (35), 95 (31), 101 (93), 109 (51), 152 (59), 194 (100), 237 (26, M⁺).

Synthesis Example 11

(1R,2S,5R,6S,7R)-2-isopropyl-5-methyl-bicyclo[4.1.0]heptane-7-carboxylic acid dimethylamide/(1S,2S,5R,6R,7S)-2-isopropyl-5-methyl-bicyclo[4.1.0]heptane-7-carboxylic acid dimethylamide The aforementioned substance was prepared according to the general synthesis procedure, using (3S,6R)-3-isopropyl-6-methylcyclohexene as alkene and dimethylamine as amine. After preparative HPLC an approx. 1:2 mixture of the two diastereomers is obtained.

(1S,2S,5R,6R,7S)-2-isopropyl-5-methyl-bicyclo[4.1.0]heptane-7-carboxylic acid dimethylamide
(Major Diastereomer)

MS (EI): m/z=41 (25), 55 (21), 72 (100), 81 (17), 87 (98), 88 (26), 95 (23), 109 (28), 138 (54), 180 (93), 223 (16, M⁺).

(1R,2S,5R,6S,7R)-2-isopropyl-5-methyl-bicyclo[4.1.0]heptane-7-carboxylic acid dimethylamide
(Minor Diastereomer)

MS (EI): m/z=41 (20), 55 (22), 72 (75), 81 (24), 87 (58), 95 (20), 109 (16), 138 (56), 180 (100), 223 (23, M⁺).

Example 1

Spray-Dried Composition for Producing an Umami Flavor

| 1.1 | Constituent | Amount |
|---|---|---|
| | Compound of the Formula (IVc) | 1 g |
| | Maltodextrin | 99 g |

| 1.2 | Constituent | Amount |
|---|---|---|
| | Mixture of the (1R,2S,5R,6S,7R) isomer and the (1S,2S,5R,6R,7S) isomer of 2-isopropyl-5-methyl-bicyclo[4.1.0]heptane-7-carboxylic acid ethylamide (Fraction A from Synthesis Example 1c) | 2 g |
| | Maltodextrin | 98 g |

The constituents are dissolved in a mixture of ethanol and demineralized water and then spray-dried.

Example 2

Spice Containing a Compound for Producing an Umami Flavor as Well as an Aroma Composition

| Part | Constituent | Amount |
|---|---|---|
| A | Compound of the Formula (IVc) | 0.01 g |
| | Sodium chloride | 15 g |
| B | Ground mustard seeds | 5 g |
| | Mustard aroma | 0.1 g |

Part A was weighed out. 290 ml of water were placed in a vessel and Part A was added and dissolved while stirring. The solution is diluted with water to 1.84 kg (pH 6.0) and then freeze-dried (eutectic point: −15° C.; operating vacuum: 0.52 mbar; shelf temperature: −5° C. to +25° C.). The product is mixed with ground mustard seeds and the mustard aroma from Part B and formulated into a spice.

Example 3

Umami Type Reaction Aroma

| Constituent | Amount [g] |
|---|---|
| L-alanine | 41 |
| L-aspartic acid | 123 |
| Succinic acid | 4.7 |
| Calcium chloride dihydrate | 7 |
| L-cysteine•HCl monohydrate | 11 |
| Dipotassium phosphate | 6 |
| Ground fructose | 1 |
| L-isoleucine | 1.6 |
| Potassium chloride | 228 |
| L-leucine | 1.6 |
| L-lysine•HCl | 3.6 |
| Magnesium chloride hexahydrate | 19 |
| Maltodextrin | 49 |
| L-phenylalanine | 2 |
| L-proline | 74 |
| L-serine | 6.5 |
| L-threonine | 3 |
| L-valine | 9 |
| Water | 399 |
| Compound of the Formula (IVc), 10 wt. % in EtOH | 10 |

All components are mixed at 40° C. and then heated at 85° C. for ten minutes (reflux reaction). After cooling to 40° C. the reaction mixture is adjusted to pH 5 with potassium hydroxide solution. This umami reaction aroma instead of the pure compound (IVc) was incorporated into the bouillon preparations C and D of application Example 5, 12 g of the umami reaction aroma being used in preparation C and 28 g of the umami reaction aroma being used in preparation D.

Application Example 1

Instant Soup, Cream of Leek Type

| Constituent | Comparison Preparation A | Preparation B according to the invention | Preparation C according to the invention | Preparation D according to the invention |
|---|---|---|---|---|
| Potato starch | 20.0 g | 21.0 g | 21.0 g | 21.0 g |
| Powdered fat | 25.0 g | 26.0 g | 26.0 g | 26.0 g |
| Lactose | 20.0 g | 21.0 g | 21.0 g | 21.0 g |
| Maltodextrin | 11.73 g | 11.727 g | 11.70 g | 11.43 g |
| Cooking salt | 8.0 g | 8.0 g | 8.0 g | 8.0 g |
| Sodium glutamate | 3.0 g | — | — | — |
| Spinach powder | 2.0 g | 2.0 g | 2.0 g | 2.0 g |
| Green leek powder | 2.0 g | 2.0 g | 2.0 g | 2.0 g |

| Constituent | Comparison Preparation A | Preparation B according to the invention | Preparation C according to the invention | Preparation D according to the invention |
|---|---|---|---|---|
| Citric acid, as powder | 0.3 g | 0.3 g | 0.3 g | 0.3 g |
| Hardened vegetable fat | 3.0 g | 3.0 g | 3.0 g | 3.0 g |
| Freeze-dried leek | 1.0 g | 1.0 g | 1.0 g | 1.0 g |
| Chicken aroma | 1.0 g | 1.0 g | 1.0 g | 1.0 g |
| "Green leek" spice mixture in powder form | 2.0 g | 2.0 g | 2.0 g | 2.0 g |
| "Boiled onion" spice mixture | 0.6 g | 0.6 g | 0.6 g | 0.6 g |
| "Vegetable stock" yeast-spice mixture in powder form | 0.3 g | 0.3 g | 0.3 g | 0.3 g |
| *Curcuma* extract | 0.07 g | 0.07 g | 0.07 g | 0.07 g |
| Compound of the Formula (IVc) | — | 0.003 g | 0.03 g | 0.30 g |

5 g of the respective powder mixture were added in each case to 100 ml of water so as to obtain a ready-to-serve soup.

In the evaluation by a panel of trained testers the comparison preparation A and the preparation C according to the invention were awarded the same scores. In the case of the preparation B according to the invention the umami taste (and mouthfeel) were described as recognizable, but less strong compared to the preparations A and C. The preparation D according to the invention was judged to have a very pronounced umami taste (and mouthfeel) and was awarded a much higher score than the preparations A and C.

Application Example 2

Instant Soup, Chicken Soup with Noodles Type

| Constituent | Comparison Preparation A | Preparation B according to the invention | Preparation C according to the invention | Preparation D according to the invention |
|---|---|---|---|---|
| Starch | 16 g | 17.2 g | 17.2 g | 17.2 g |
| Cooking salt | 7 g | 7 g | 7 g | 7 g |
| Refined sucrose | 3.2 g | 3.2 g | 3.2 g | 3.2 g |
| Sodium glutamate | 3.2 g | — | — | — |
| Sodium inosinate/sodium guanylate in the ratio 1:1 | 0.8 g | 0.8 g | 0.8 g | 0.8 g |
| Acid-hydrolysed vegetable protein | 8.0 g | 8.0 g | 8.0 g | 8.0 g |
| Powdered fat | 2.0 g | 2.0 g | 2.0 g | 2.0 g |
| Spray-dried vegetable fat | 1.0 g | 1.0 g | 1.0 g | 1.0 g |
| Freeze-dried chicken meat, in small pieces | 2.0 g | 2.0 g | 2.0 g | 2.0 g |
| Soup noodles | 32.0 g | 33.0 g | 33.0 g | 33.0 g |
| Maltodextrin | 12.16 g | 13.157 g | 13.13 g | 12.86 g |
| Freeze-dried Chinese vegetables | 4.6 g | 4.6 g | 4.6 g | 4.6 g |
| Chicken aroma | 8.0 g | 8.0 g | 8.0 g | 8.0 g |
| Food colouring agent riboflavin | 0.04 g | 0.04 g | 0.04 g | 0.04 g |
| Compound of the Formula (IVc) | — | 0.003 g | 0.03 g | 0.3 g |

4.6 g of the respective powder mixture were boiled for 10 minutes in in each case 100 ml of water in order to obtain a ready-to-serve soup.

In the evaluation by a panel of trained testers the comparison preparation A and the preparation C according to the invention were awarded the same scores. In the case of the preparation B according to the invention the umami taste (and mouthfeel) were described as recognizable, but less strong compared to the preparations A and C. The preparation D according to the invention was judged to have a very pronounced umami taste (and mouthfeel) and was awarded a much higher score than the preparations A and C.

Application Example 3

"Pepper" Type Spice Mixture

| Constituent | Comparison Preparation A | Preparation B according to the invention | Preparation C according to the invention | Preparation D according to the invention |
|---|---|---|---|---|
| Milk protein | 0.8 g | 0.8 g | 0.8 g | 0.8 g |
| Carob seed flour | 2.0 g | 2.0 g | 2.0 g | 2.0 g |
| Maize (corn) starch | 25.0 g | 26.994 g | 26.94 g | 26.4 g |
| Cooking salt | 14.0 g | 15.0 g | 15.0 g | 15.0 g |
| Paprika powder | 12.0 g | 13.0 g | 13.0 g | 13.0 g |
| Tomato powder | 12.0 g | 13.0 g | 13.0 g | 13.0 g |
| Sucrose | 4.0 g | 4.0 g | 4.0 g | 4.0 g |
| Garlic powder | 0.5 g | 0.5 g | 0.5 g | 0.5 g |
| Hardened vegetable fat | 8.0 g | 8.0 g | 8.0 g | 8.0 g |
| Powdered fat | 10.0 g | 11.0 g | 11.0 g | 11.0 g |
| Sodium glutamate | 6.0 g | — | — | — |
| Foodstuff colouring agent Red beetroot and Paprika | 2.0 g | 2.0 g | 2.0 g | 2.0 g |
| "Pepper" type aroma | 2.0 g | 2.0 g | 2.0 g | 2.0 g |
| "Pizza" type aroma | 1.2 g | 1.2 g | 1.2 g | 1.2 g |
| "Tomato" type aroma | 0.4 g | 0.4 g | 0.4 g | 0.4 g |
| Extract of black pepper | 0.1 g | 0.1 g | 0.1 g | 0.1 g |
| Compound of the Formula (IVc) | — | 0.006 g | 0.06 g | 0.6 g |

1.7 g of each of the preparations A, B, C and D were in each case uniformly sprinkled over 100 g of pork neck cutlets and pan-fried. In the evaluation by a panel of trained testers the comparison preparation A and the preparation C according to the invention were awarded the same score. With the preparation B according to the invention the umami taste (mouthfeel) was described as recognizable, but not as pronounced as in the case of the preparations A and C. The preparation D according to the invention was judged to have a very pronounced umami taste (mouthfeel) and was awarded a much higher score than the preparations A and C.

Application Example 4

Tomato Ketchup

| Constituent | Comparison Preparation A | Preparation B according to the invention | Preparation C according to the invention |
|---|---|---|---|
| Sodium glutamate | 6 g | — | — |
| Cooking salt | 2 g | 2 g | 2 g |
| Starch, Farinex WM 55 | 1 g | 1 g | 1 g |
| Sucrose | 12 g | 12 g | 12 g |
| Tomato concentrate ×2 | 36 g | 36 g | 36 g |
| Glucose syrup 80 Brix | 18 g | 18 g | 18 g |
| Brandy vinegar 10% | 7 g | 7 g | 7 g |
| Water | 18 g | 23.8 g | 23.5 g |
| Compound of the Formula (P1) & (P2) in the ratio 3:2 | — | 0.2 g | 0.5 g |

The ingredients are mixed in the specified order and the ready ketchup is homogenized by means of a stirrer, filled in bottles and sterilized.

Application Example 5

Bouillon

| Constituent | Comparison preparation A | Sodium glutamate-reduced Comparison Preparation B | Sodium glutamate-reduced Preparation C according to the invention | Sodium glutamate-free Preparation D according to the invention |
|---|---|---|---|---|
| Powdered fat | 8.77 g | 8.77 g | 8.77 g | 8.77 g |
| Sodium glutamate | 8.77 g | 5 g | 5 g | — |
| Powdered yeast extract | 12.28 g | 12.28 g | 12.28 g | 12.28 g |
| Cooking salt | 29.83 g | 29.83 g | 29.83 g | 29.83 g |
| Maltodextrin | 37.28 g | 37.28 g | 37.28 g | 37.28 g |
| Natural vegetable extract | 3.07 g | 3.07 g | 3.07 g | 3.07 g |
| Compound of the Formula (IVc) | — | — | 0.05 g | 0.12 g |

15 g of the respective powder mixture were added in each case to 1000 ml of hot water. For the evaluation the preparations were evaluated by 5 to 8 testers and the umami taste was awarded a point score ranging from 0 (no detectable umami taste) to 9 (extremely pronounced umami taste). The aqueous comparison solutions containing only sodium glutamate listed in the following table were used as reference samples for the umami detection.

| | sodium glutamate in % | | | | | | | | |
|---|---|---|---|---|---|---|---|---|---|
| | 0 | 0.03 | 0.05 | 0.07 | 0.09 | 0.11 | 0.12 | 0.13 | 0.14 | 0.15 |
| Intensity | 0 | 1 | 2 | 3 | 4 | 5 | 6 | 7 | 8 | 9 |

Each preparation to be evaluated was tested individually against the comparison solutions of the reference series.

| | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Umami taste (0-9) | 3.4 ± 0.8 | 1.9 ± 0.7 | 3.0 ± 0.8 | 3.2 ± 0.6 |

Application Example 6

Spice Mixture for Potato Crisps

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Sodium glutamate | 3.50 g | 2 g | 2 g | — |

-continued

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Cheese powder | 10.00 g | 10.00 g | 10.00 g | 10.00 g |
| Garlic powder | 2.00 g | 2.00 g | 2.00 g | 2.00 g |
| Whey powder | 38.86 g | 38.86 g | 38.86 g | 38.86 g |
| Spice extract oil | 0.20 g | 0.20 g | 0.20 g | 0.20 g |
| Paprika powder | 9.80 g | 9.80 g | 9.80 g | 9.80 g |
| Cooking salt | 21.00 g | 21.00 g | 21.00 g | 21.00 g |
| Tomato powder | 9.00 g | 9.00 g | 9.00 g | 9.00 g |
| Dry aroma | 2.50 g | 2.50 g | 2.50 g | 2.50 g |
| Silicon dioxide | 0.02 g | 0.02 g | 0.02 g | 0.02 g |
| Vegetable oil | 0.02 g | 0.02 g | 0.02 g | 0.02 g |
| Onion powder | 3.00 g | 3.00 g | 3.00 g | 3.00 g |
| Cream aroma concentrate | 0.03 g | 0.03 g | 0.03 g | 0.03 g |
| Cheese aroma | 0.03 g | 0.03 g | 0.03 g | 0.03 g |
| Tomato aroma concentrate | 0.04 g | 0.04 g | 0.04 g | 0.04 g |
| Spray-dried composition according to Example 1 | — | — | 1.40 g | 2.70 g |

6 g of the spice mixture were sprinkled on 94 g of potato crisps. The evaluation of the umami taste was carried out similarly to Application Example 1.

| | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Umami taste (0-9) | 3.4 ± 0.9 | 2.4 ± 0.6 | 3.5 ± 0.6 | 3.4 ± 0.7 |

Application Example 7

White Sauce

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Maltodextrin | 26.28 g | 26.28 g | 26.28 g | 26.28 g |
| Cooking salt | 7.50 g | 7.50 g | 7.50 g | 7.50 g |
| Sodium glutamate | 2.00 g | 0.80 g | 0.80 g | — |
| Vegetable fat | 5.00 g | 5.00 g | 5.00 g | 5.00 g |
| White pepper | 0.02 g | 0.02 g | 0.02 g | 0.02 g |
| Onion powder | 1.50 g | 1.50 g | 1.50 g | 1.50 g |
| Pre-gelatinized corn starch | 30.00 g | 30.00 g | 30.00 g | 30.00 g |
| Powdered fat | 27.70 g | 27.70 g | 27.70 g | 27.70 g |
| Spray-dried composition according to Example 1.2 | — | — | 1.00 g | 1.80 g |

90 g of the sauce mixture were added to 1000 ml of hot water and vigorously stirred with a whisk. The evaluation of the umami taste was carried out in a similar way to Application Example 1.

|  | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Umami taste (0-9) | 3.5 ± 0.7 | 2.3 ± 0.5 | 3.5 ± 1.0 | 3.6 ± 0.6 |

Application Example 8

Brown Sauce

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Starch | 40.00 g | 40.00 g | 40.00 g | 40.00 g |
| Maltodextrin | 33.10 g | 33.10 g | 33.10 g | 33.10 g |
| Cooking salt | 6.00 g | 6.00 g | 6.00 g | 6.00 g |
| Spray-dried sugar coloring | 5.00 g | 5.00 g | 5.00 g | 5.00 g |
| Yeast extract powder | 3.00 g | 3.00 g | 3.00 g | 3.00 g |
| Sodium glutamate | 2.00 g | 1.30 g | 1.30 g | — |
| Sugar | 0.50 g | 0.50 g | 0.50 g | 0.50 g |
| Powdered fat | 5.00 g | 5.00 g | 5.00 g | 5.00 g |
| Tomato powder | 3.00 g | 3.00 g | 3.00 g | 3.00 g |
| Natural vegetable extract | 1.00 g | 1.00 g | 1.00 g | 1.00 g |
| Onion extract | 0.30 g | 0.30 g | 0.30 g | 0.30 g |
| Pepper extract | 0.10 g | 0.10 g | 0.10 g | 0.10 g |
| Dry aroma | 1.00 g | 1.00 g | 1.00 g | 1.00 g |
| Spray-dried composition according to Example 1.2 | — | — | 0.70 g | 2.00 g |

90 g of the sauce mixture were added to 1000 ml of hot water and vigorously stirred with a whisk. The evaluation of the umami taste was carried out in a similar way to Application Example 1.

|  | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Umami taste (0-9) | 5.2 ± 1.0 | 3.7 ± 1.3 | 5.1 ± 1.2 | 4.8 ± 1.3 |

Application Example 9

Tomato Soup

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Water | 50.65 g | 50.65 g | 50.65 g | 50.65 g |
| Vegetable oil | 5.50 g | 5.50 g | 5.50 g | 5.50 g |
| Tomato paste | 24.00 g | 24.00 g | 24.00 g | 24.00 g |

-continued

| Constituent | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Cream | 1.05 g | 1.05 g | 1.05 g | 1.05 g |
| Sugar | 2.00 g | 2.00 g | 2.00 g | 2.00 g |
| Cooking salt | 1.70 g | 1.70 g | 1.70 g | 1.70 g |
| Sodium glutamate | 0.40 g | 0.25 g | 0.25 g | — |
| Wheat flour | 5.50 g | 5.50 g | 5.50 g | 5.50 g |
| Starch | 1.20 g | 1.20 g | 1.20 g | 1.20 g |
| Chopped tomatoes | 8.00 g | 8.00 g | 8.00 g | 8.00 g |
| Spray-dried composition according to Example 1.2 | — | — | 0.20 g | 0.40 g |

The solid ingredients were weighed out, mixed, and added to the water. The vegetable oil was poured in and the tomato paste was added. The mixture was boiled while stirring. The evaluation of the umami taste was carried out in a similar way to Application Example 1.

| | Comparison Preparation A | Sodium glutamate-reduced Comparison Preparation B | Sodium glutamate-reduced Preparation C according to the invention | Sodium glutamate-free Preparation D according to the invention |
|---|---|---|---|---|
| Umami taste (0-9) | 5.2 ± 0.8 | 3.3 ± 0.9 | 5.6 ± 1.0 | 5.7 ± 1.2 |

Application Example 10

Use in a Sugar-Free Chewing Gum

| Part 1 | Constituent | Amount in wt. % |
|---|---|---|
| A | Chewing gum base, "Jagum T" Company | 30.00 |
| B | Powdered sortibol | 39.00 |
| | Isomalt ® (Palatinit GmbH) | 9.50 |
| | Xylitol | 2.00 |
| | Mannitol | 3.00 |
| | Aspartam ® | 0.10 |
| | Acesulfam ® K | 0.10 |
| | Emulgum ® (Colloides Naturels, Inc.) | 0.30 |
| C | Sorbitol, 70% | 14.00 |
| | Glycerol | 1.00 |
| D | Aroma composition containing 0.1 wt. % (2E,4E)-deca-2,4-dienoic acid isobutyl-amide and 10 wt. % of a mixture of the compounds of the Formulae (P1) & (P2) in a 3:2 ratio | 1 |

Parts A to D were mixed and intensively kneaded. The raw composition can be processed for example in the form of thin strips into ready-to-use chewing gum.

Specific Embodiments

Specific embodiment one comprises use of a compound of the Formula (I)

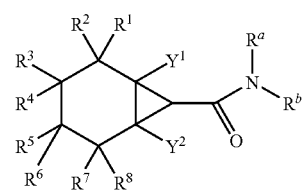

(I)

wherein:
$R^1$, $R^2$, $R^3$, $R^4$, $R^5$, $R^6$, $R^7$ and $R^8$ denote in each case independently of one another hydrogen, an alkyl radical with 1 to 6 C atoms, or an alkenyl radical with 2 to 6 C atoms,
with the proviso that at least one of the radicals $R^1$, $R^2$, $R^7$ and $R^8$ and at least one further of the radicals $R^1$, $R^2$, $R^3$, $R^4$, $R^5$, $R^6$, $R^7$ and $R^8$ are not hydrogen, wherein independently of one another also two of the radicals $R^1$, $R^2$, $R^3$, $R^4$, $R^5$, $R^6$, $R^7$ and $R^8$ can together denote a bridge with one or more bridge C atoms;
$Y^1$ and $Y^2$ denote independently of one another hydrogen, methyl or ethyl;
and
$R^a$ and $R^b$ denote independently of one another hydrogen, an alkyl radical with 1 to 6 C atoms, an alkenyl radical with 2 to 6 C atoms or a cycloalkyl radical with 3 to 6 C atoms as a food flavor substance.

Specific embodiment two comprises use according to specific embodiment one, wherein three, four, five or six of the radicals $R^1$, $R^2$, $R^3$, $R^4$, $R^5$, $R^6$, $R^7$ and $R^8$ denote hydrogen.

Specific embodiment three comprises use according to one of the preceding specific embodiments, wherein the total number of carbon atoms of the compound of the Formula (I) is not greater than 25, preferably not greater than 20.

Specific embodiment four comprises use according to one of the preceding specific embodiments, wherein the compound of the Formula (I) is a compound of the Formula (II),

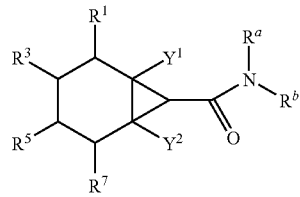
(II)

wherein;

$R^1$, $R^3$, $R^5$ and $R^7$ denote in each case independently of one another hydrogen, an alkyl radical with 1 to 6 C atoms or an alkenyl radical with 2 to 6 C atoms, with the proviso that at least one of the radicals $R^1$ and $R^7$ and a further one of the radicals $R^1$, $R^3$, $R^5$ and $R^7$ are not hydrogen, wherein independently of one another also two of the radicals $R^1$, $R^3$, $R^5$ and $R^7$ may jointly form a bridge with one or more bridge C atoms, $Y^1$ and $Y^2$ denote independently of one another hydrogen, methyl or ethyl, and $R^a$ and $R^b$ denote independently of one another hydrogen, an alkyl radical with 1 to 6 C atoms, an alkenyl radical with 2 to 6 C atoms or a cycloalkyl radical with 3 to 6 C atoms.

Specific embodiment five comprises use according to one of the preceding specific embodiments, wherein:

$Y^1$ and $Y^2$ denote independently of one another hydrogen or methyl, and preferably both denote hydrogen.

Specific embodiment six comprises use according to one of the preceding specific embodiments, wherein the compound of the Formula (I)

is a compound of the formula (III)

wherein:

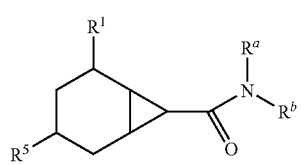

$R^1$ and $R^5$ denote independently of one another in each case an alkyl radical with 1 to 6 C atoms or jointly denote a bridge with one or more bridge C atoms, or is a compound of the Formula (IV)

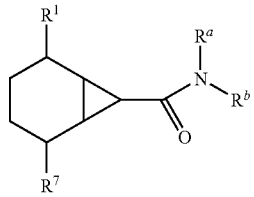
(IV)

wherein:

$R^1$ and $R^7$ denote independently of one another in each case an alkyl radical with 1 to 6 C atoms or jointly denote a bridge with one or more bridge C atoms, wherein in Formula (III) and Formula (IV):

$R^a$ and $R^b$ denote independently of one another hydrogen, an alkyl radical with 1 to 6 C atoms, an alkenyl radical with 2 to 6 C atoms or a cycloalkyl radical with 3 to 6 C atoms.

Specific embodiment seven comprises use according to specific embodiment six, wherein $R^1$ and $R^5$ in Formula (III) as well as $R^1$ and $R^7$ in Formula (IV)

denote independently of one another in each case methyl, ethyl, n-propyl, iso-propyl, n-butyl, iso-butyl, sec.-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl or 1,2,2-trimethyl-propyl, or denote jointly a —$CH_2$—, —$C(CH_3)_2$—, $CH_2CH_2$— or CH=CH— bridge.

Specific embodiment eight comprises use according to specific embodiment six or seven, wherein:

$R^a$ and $R^b$ denote independently of one another hydrogen or an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methyl-butyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethyl-butyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl or an alkenyl radical with 2 to 6 C atoms or a cycloalkyl radical with 3 to 6 C atoms, wherein preferably $R^b$ denotes ethyl, cyclopropyl, cyclobutyl, cyclopentyl or cyclohexyl.

Specific embodiment nine comprises use according to one of specific embodiment six to eight, wherein:

$R^a$ denotes hydrogen and $R^b$ denotes an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methylbutyl, 2-methyl-butyl, 3-methylbutyl, 1,2-dimethylpropyl, 1,1-dimethylpropyl, 2,2-dimethylpropyl, n-hexyl, 1-methyl-pentyl, 2-methylpentyl, 3-methylpentyl, 4-methyl-pentyl, 1-ethylbutyl, 2-ethylbutyl, 1,1-dimethyl-butyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl, or an alkenyl radical with 2 to 6 C atoms or a cycloalkyl radical with 3 to 6 atoms, wherein preferably $R^b$ denotes ethyl, cyclopropyl, cyclobutyl, cyclopentyl or cyclohexyl or $R^a$ and $R^b$ both denote methyl.

Specific embodiment ten comprises use according to one of specific embodiments six to nine, wherein the compound of the Formula (IV) is a compound of the Formula (IVa), preferably one of the two enantiomeric compounds of the Formula (Iva)

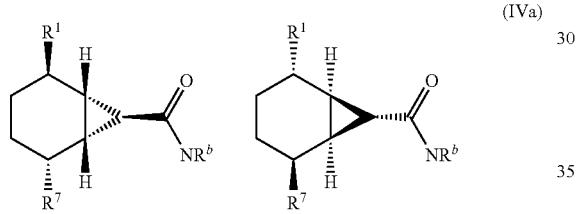

(IVa)

Specific embodiment eleven comprises use according to one of specific embodiments six to ten, wherein the compound of the Formula (IV) is a compound of the Formula (IVc).

Specific embodiment twelve comprises use according to one of the specific embodiments one to nine, wherein the compound of the Formula (IV) is a compound of the Formula (E1) and/or (E2)

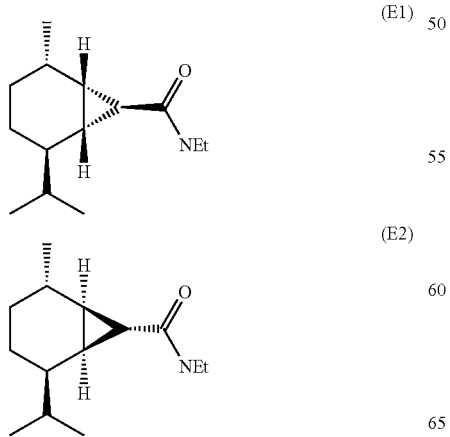

and/or a compound of the Formula (B1) and/or (B2)

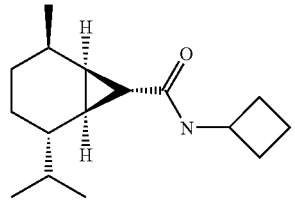

(B1)

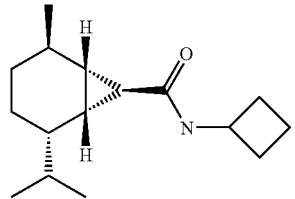

(B2)

and/or a compound of the Formula (P1) and/or (P2)

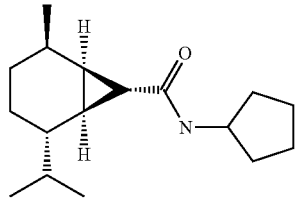

(P1)

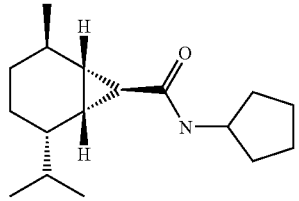

(P2)

and/or a compound of the Formula (P3) and/or (P4)

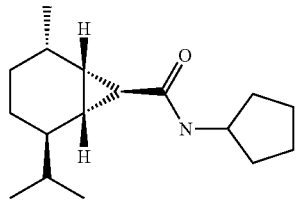

(P3)

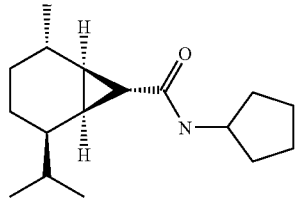

(P4)

and/or a compound of the Formula (H1) and/or (H2)

(H1)

(H2)

Specific embodiment thirteen comprises use of a compound of the Formulae (I), (II), (III) or (IV) as defined in one of the preceding specific embodiments, for producing, modifying or intensifying an umami taste.

Specific embodiment fourteen comprises a composition suitable for consumption, containing or consisting of
- a taste-active amount of one or more compounds of the Formula (I), (II), (III) or (IV) as defined in one of specific embodiments one to twelve, as well as
- one or more further ingredients suitable for consumption.

Specific embodiment fifteen comprises a composition according to specific embodiment fourteen, wherein the further ingredients are:
- solid carrier substances or
- solid carrier substances and aroma compositions, or
- water, an oily phase, one or more W/O emulsifiers, optionally one or more antioxidants and optionally one or more substances for intensifying an antioxidative action.

Specific embodiment sixteen comprises a composition according to specific embodiment fifteen, wherein the further ingredients are solid carrier substances and the weight ratio of the total mass of the compounds of the Formulae (I), (II), (III) or (IV) as defined in one of specific embodiments one to twelve to the solid carrier substances is in the range from 1:10 to 1:100000, preferably in the range from 1:100 to 1:20000, particularly preferably in the range from 1:1000 to 1:5000, referred to the dry mass of the composition.

Specific embodiment seventeen comprises a composition according to specific embodiment fifteen, including or consisting of
- 0.01 to 0.1 wt. % of one or more compounds of the Formulae (I), (II), (III) or (IV) as defined in one of specific embodiments one to twelve,
- 5 to 30 wt. % of water,
- 50 to 90 wt. % of an oily phase,
- 0.1 to 5 wt. % of an edible W/O emulsifier, as well as
- optionally one or more antioxidants and optionally one or more substances for intensifying an antioxidative action.

18. (i) ready-for-use or ready-to-eat preparation or (ii) semi-finished product serving for nutritional or consumption purposes, including
- a taste-active amount of one or more compounds of the Formulae (I), (II), (III) or (IV) as defined in one of specific embodiments one to twelve, or
- a composition according to one of specific embodiments fourteen to seventeen.

Specific embodiment nineteen comprises ready-for-use or ready-to-eat preparation according to specific embodiment eighteen serving for nutritional or consumption purposes, comprising 0.01 ppm to 100 ppm, preferably 0.1 ppm to 50 ppm, particularly preferably 1 ppm to 30 ppm of one or more of the compounds of the Formulae (I), (II), (III) or (IV) as defined in one of the specific embodiments one to twelve, referred to the total weight of the ready-to-eat preparation.

Specific embodiment twenty comprises a composition, preparation or semi-finished product according to one of specific embodiments fourteen to nineteen, including in addition a substance for masking or reducing an unpleasant taste impression and/or a substance for intensifying the pleasant taste impression of a pleasantly tasting substance.

Specific embodiment twenty-one comprises process for producing, modifying or intensifying a taste in a (i) ready-to-eat preparation or (ii) semi-finished product serving for nutritional or consumption purposes, comprising the following step:
- mixing a taste-active amount of one or more compounds of the Formulae (I), (II), (III) or (IV) as defined in one of specific embodiments one to twelve or a composition according to one of specific embodiments fourteen to seventeen or twenty with one or more further ingredients of the (i) ready-to-eat preparation or of the (ii) semi-finished product, or
- adding a taste-active amount of one or more compounds of the Formulae (I), (II), (III) or (IV) as defined in one of the specific embodiments one to twelve or a composition according to one of specific embodiments fourteen to seventeen or twenty to one or more further ingredients of the (i) ready-to-eat preparation or of the (ii) semi-finished product, or
- embedding a taste-active amount of one or more compounds of the Formulae (I), (II), (III) or (IV) as defined in one of the specific embodiments one to twelve or a composition according to one of specific embodiments fourteen to seventeen or twenty in a shell or matrix material.

Specific embodiment twenty-two comprises a process according to specific embodiment twenty-one, for producing, modifying or intensifying an umami taste.

Specific embodiment twenty-three comprises a compound of the Formula (I)

(I)

wherein:
$R^1$, $R^2$, $R^3$, $R^4$, $R^5$, $R^6$, $R^7$ and $R^8$ denote in each case independently of one another hydrogen, an alkyl radical with 1 to 6 C atoms, or an alkenyl radical with 2 to 6 C atoms,
with the proviso that at least one of the radicals $R^1$, $R^2$, $R^7$ and $R^8$ and at least a further one of the radicals $R^1$, $R^2$, $R^3$, $R^4$, $R^5$, $R^6$, $R^7$ and $R^8$ are not hydrogen, wherein independently of one another also two of the radicals $R^1$, $R^2$, $R^3$, $R^4$, $R^5$, $R^6$, $R^7$ and $R^8$ can together denote a bridge with one or more bridge C atoms;

$Y^1$ and $Y^2$ denote independently of one another hydrogen, methyl or ethyl;

and $R^a$ and $R^b$ denote independently of one another hydrogen, an alkyl radical with 1 to 6 C atoms, an alkenyl radical with 2 to 6 C atoms or a cycloalkyl radical with 3 to 6 C atoms, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide; (1R,2R,4R,7R)-4,8,8-trimethyltricyclo[5.1.0.0$^{2,4}$]octane-3-carboxylic acid amide; 2,7,7-trimethyltricyclo[4.1.1.0$^{2,4}$]octane-3-carboxylic acid amide and 4,7,7-trimethyltricyclo[4.1.1.0$^{2,4}$]octane-3-carboxylic acid amide.

Specific embodiment twenty-four comprises a compound according to specific embodiment twenty-three, wherein three, four, five or six of the radicals $R^1$, $R^2$, $R^3$, $R^4$, $R^5$, $R^6$, $R^7$ and $R^8$ denote hydrogen, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide; (1R,2R,4R,7R)-4,8,8-trimethyltricyclo[5.1.0.0$^{2,4}$]octane-3-carboxylic acid amide; 2,7,7-trimethyltricyclo[4.1.1.0$^{2,4}$]octane-3-carboxylic acid amide and 4,7,7-trimethyltricyclo[4.1.1.0$^{2,4}$]octane-3-carboxylic acid amide.

Specific embodiment twenty-five comprises a compound according to one of specific embodiments twenty-three and twenty-four, wherein the total number of carbon atoms of the compound of the Formula (I) is not greater than 25, and is preferably not greater than 20, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide; (1R,2R,4R,7R)-4,8,8-trimethyltricyclo[5.1.0.0$^{2,4}$]octane-3-carboxylic acid amide; 2,7,7-trimethyltricyclo[4.1.1.0$^{2,4}$]octane-3-carboxylic acid amide and 4,7,7-trimethyltricyclo[4.1.1.0$^{2,4}$]octane-3-carboxylic acid amide.

Specific embodiment twenty-six comprises a compound according to one of specific embodiments twenty-three to twenty-five, wherein the compound of the Formula (I) is a compound of the Formula (II),

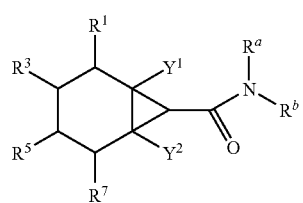

(II)

wherein;

$R^1$, $R^3$, $R^5$ and $R^7$ denote in each case independently of one another hydrogen, an alkyl radical with 1 to 6 C atoms or an alkenyl radical with 2 to 6 C atoms, with the proviso that at least one of the radicals $R^1$ and $R^7$ and a further one of the radicals $R^1$, $R^3$, $R^5$ and $R^7$ are not hydrogen, wherein independently of one another also two of the radicals $R^1$, $R^3$, $R^5$ and $R^7$ may jointly form a bridge with one or more bridge C atoms, $Y^1$ and $Y^2$ denote independently of one another hydrogen, methyl or ethyl, and $R^a$ and $R^b$ denote independently of one another hydrogen, an alkyl radical with 1 to 6 C atoms, an alkenyl radical with 2 to 6 C atoms or a cycloalkyl radical with 3 to 6 C atoms, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide and (1R,2R,4R,7R)-4,8,8-trimethyltricyclo[5.1.0.0$^{2,4}$]octane-3-carboxylic acid amide.

Specific embodiment twenty-seven comprises a compound according to one of specific embodiments twenty-three to twenty-six, wherein:

$Y^1$ and $Y^2$ denote independently of one another hydrogen or methyl, and preferably both denote hydrogen, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide; (1R,2R,4R,7R)-4,8,8-trimethyltricyclo[5.1.0.0$^{2,4}$]octane-3-carboxylic acid amide; 2,7,7-trimethyltricyclo[4.1.1.0$^{2,4}$]octane-3-carboxylic acid amide and 4,7,7-trimethyltricyclo[4.1.1.0$^{2,4}$]octane-3-carboxylic acid amide.

Specific embodiment twenty-eight comprises a compound according to one of specific embodiments twenty-three to twenty-seven, wherein the compound of the Formula (I) is a compound of the Formula (III),

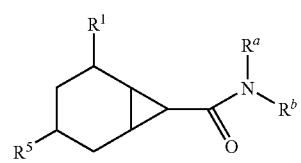

(III)

wherein:

$R^1$ and $R^5$ denote independently of one another in each case an alkyl radical with 1 to 6 C atoms or jointly denote a bridge with one or more bridge C atoms, with the exception of:

2,4-dimethylbicyclo[4.1.0]heptane-7-carboxylic acid amide;

or a compound of the Formula (IV)

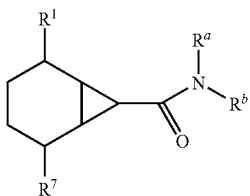
(IV)

wherein:
R[1] and R[7] denote independently of one another in each case an alkyl radical with 1 to 6 C atoms or are covalently bonded to one another, wherein in Formula (III) and Formula (IV):

R[a] and R[b] denote independently of one another hydrogen, an alkyl radical with 1 to 6 C atoms, an alkenyl radical with 2 to 6 C atoms or a cycloalkyl radical with 3 to 6 C atoms, with the exception of the compounds selected from the group consisting of:

(2S,5R)-2-isopropyl-5-methylbicyclo[4.1.0]heptane-7-carboxylic acid amide and (exo) (1R,2S,4S,5S)-tricyclo[3.2.1.0$^{2,4}$]octane-3-carboxylic acid amide.

Specific embodiment twenty-nine comprises a compound according to specific embodiment twenty-eight, wherein R[1] and R[5] in Formula (III) as well as R[1] and R[7] in Formula (IV) denote independently of one another in each case methyl, ethyl, n-propyl, iso-propyl, n-butyl, iso-butyl, sec.-butyl, tert.-butyl, n-pentyl, 1-methylbutyl, 2-methyl-butyl, 3-methylbutyl, 1,2-dimethylpropyl, 1,1-dimethyl-propyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl or 1,2,2-trimethylpropyl, or together denote a —CH$_2$—, —C(CH$_3$)$_2$—, CH$_2$CH$_2$— or CH=CH— bridge, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide and (exo) (1R,2S,4S,5S)-tricyclo[3.2.1.0$^{2,4}$]octane-3-carboxylic acid amide.

Specific embodiment thirty comprises a compound according to one of specific embodiment twenty-eight or twenty-nine, wherein:

R[a] and R[b] denote independently of one another hydrogen or an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethyl-propyl and 1,2,2-trimethylpropyl or an alkenyl radical with 2 to 6 C atoms or a cycloalkyl radical with 3 to 6 C atoms, wherein preferably R[b] denotes ethyl, cyclopropyl, cyclobutyl, cyclopentyl or cyclohexyl with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide and (exo) (1R,2S,4S,5S)-tricyclo[3.2.1.0$^{2,4}$]octane-3-carboxylic acid amide.

Specific embodiment thirty-one comprises a compound according to one of specific embodiments twenty-eight to thirty, wherein:

R[a] denotes hydrogen, and

R[b] denotes an alkyl radical with 1 to 6 C atoms, selected from the group consisting of methyl, ethyl, n-propyl, iso-propyl, n-butyl, iso-butyl, sec.-butyl, tert.-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl, or an alkenyl radical with 2 to 6 C atoms or a cycloalkyl radical with 3 to 6 atoms, preferably wherein preferably R[b] denotes ethyl, cyclopropyl, cyclobutyl, cyclopentyl or cyclohexyl.

or

R[a] and R[b] both denote methyl.

Specific embodiment thirty-two comprises a compound according to one of specific embodiments twenty-eight to thirty-one, wherein the compound of the Formula (IV) is a compound of the Formula (IVa), preferably one of the two enantiomeric compounds of the Formula (IVa)

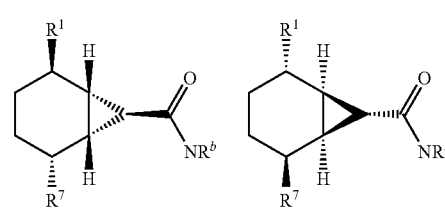
(IVa)

Specific embodiment thirty-three comprises a compound according to one of specific embodiments twenty-eight to thirty-two, wherein the compound of the Formula (IV) is a compound of the Formula (IVc)

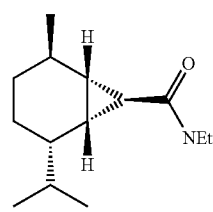
(IVc)

Specific embodiment thirty-four comprises a compound according to one of specific embodiments twenty-eight to thirty, wherein the compound of the Formula (IV) is a compound of the Formula (E1) and/or (E2)

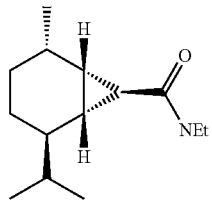
(E1)

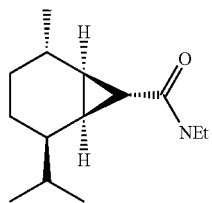
(E2)

and/or (B1) and/or (B2)

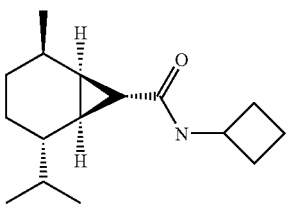
(B1)

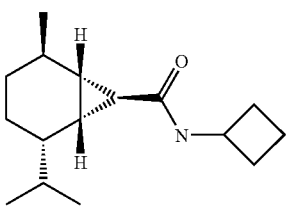
(B2)

and/or (P1) and/or (P2)

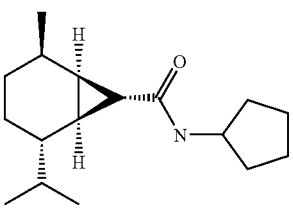
(P1)

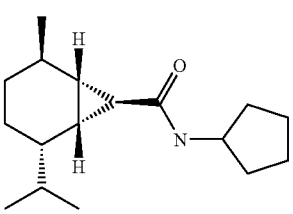
(P2)

and/or (P3) and/or (P4)

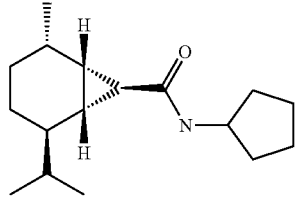
(P3)

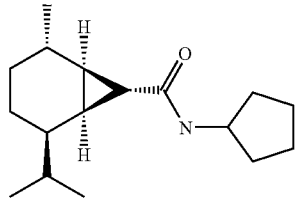
(P4)

and/or (H1) and/or (H2)

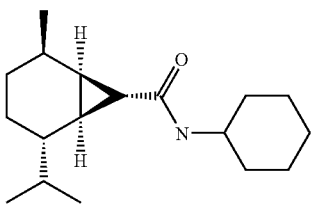
(H1)

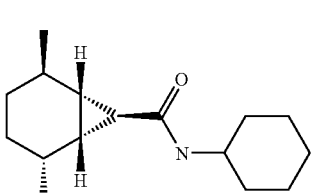
(H2)

Specific embodiment thirty-five comprises a process for the production of a compound of the Formulae (IVa) or (IVc) as defined in one of specific embodiments thirty-two or thirty-three, comprising the following steps:

Reacting a compound of the Formula (V)

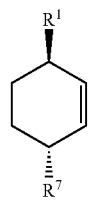
(V)

with a compound capable of forming a carbene, whereby a compound of the Formula (VI) is formed

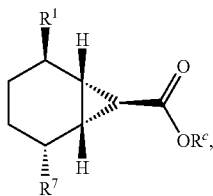
(VI)

wherein: $R^c$ denotes alkyl, preferably ethyl,
saponification of the compound of the Formula (VI) to form a compound of the Formula (VII)

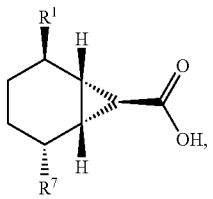
(VII)

conversion of the compound of the Formula (VII) to the corresponding acid chloride and subsequent reaction of the acid chloride with a compound of the Formula $NH_2-R^b$,
wherein $R^1$, $R^7$ and $R^b$ have the meanings given above.

Specific embodiment thirty-six comprises a process for the production of a compound of the Formula
(i) (E1) and/or (E2)
(ii) (B1) and/or (B2)
(iii) (P1), (P2), (P3) and/or (P4)
(iv) (H1) and/or (H2)
as defined in specific embodiment thirty-four, comprising the following steps:
reacting a compound of the Formula (V)

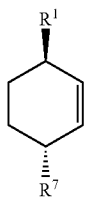
(V)

with a compound capable of forming a carbene, whereby a compound of the Formula (VI) is formed

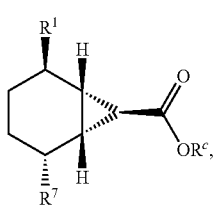
(VI)

wherein: $R^c$ denotes alkyl, preferably ethyl,
saponification of the compound of the Formula (VI) to form a compound of the Formula (VII)

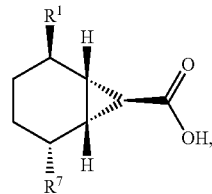
(VII)

conversion of the compound of the Formula (VII) to the corresponding acid chloride and subsequent reaction of the acid chloride with a compound of the Formula $NH_2-R^b$,
wherein $R^1$ denotes methyl
$R^7$ denotes isopropyl and
$R^b$ denotes (i) ethyl
(ii) cyclobutyl
(iii) cyclopentyl or
(iv) cyclohexyl.

It is claimed:
1. The compound of the Formula (II),

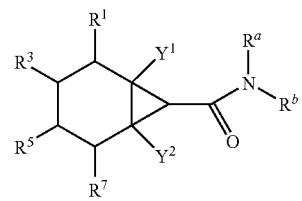
(II)

wherein;
$R^1$, $R^3$, $R^5$ and $R^7$ denote in each case independently of one another hydrogen, an alkyl radical with 1 to 6 C atoms or an alkenyl radical with 2 to 6 C atoms,
with the proviso that at least one of the radicals $R^1$ and $R^7$ and a further one of the radicals $R^1$, $R^3$, $R^5$ and $R^7$ are not hydrogen,
wherein independently of one another also two of the radicals $R^1$, $R^3$, $R^5$ and $R^7$ may jointly form a bridge with one or more bridge C atoms,
$Y^1$ and $Y^2$ denote independently of one another hydrogen, methyl or ethyl,
and
$R^a$ and $R^b$ denote independently of one another hydrogen, an alkyl radical with 1 to 6 C atoms, an alkenyl radical with 2 to 6 C atoms or a cycloalkyl radical with 3 to 6 C atoms,
with the exception of the compounds selected from the group consisting of:
2,4-dimethylbicyclo[4.1.0]heptane-7-carboxylic acid amide; (2S,5R)-2-isopropyl-5-methylbicyclo[4.1.0] heptane-7-carboxylic acid amide; (exo) (1R,2S,4S,5S)-tricyclo[3.2.1.0$^{2,4}$]octane-3-carboxylic acid amide, (1R, 2R,4R,7R)-4,8,8-trimethyltricyclo[5.1.0.0$^{2,4}$]octane-3-carboxylic acid amide, 2,7,7-trimethyltricyclo[4.1. 1.0$^{2,4}$]octane-3-carboxylic acid amide, 4,7,7-trimethyl-tricyclo[4.1.1.0$^{2,4}$]octane-3-carboxylic acid amide, (exo) (1aR,2R,2aS,5aR,6S,6aS)-decahydro-2,6-methanocyclopropa[f]indene-1-carboxamide and exo-tricyclo[3.2.1.0$^{2,4}$]octane-3-anti-carboxylic acid dimethyl amide.

2. The compound of claim 1, wherein:

Y$^1$ and Y$^2$ denote independently of one another hydrogen or methyl, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide; (exo) (1R,2S,4S,5S)-tricyclo[3.2.1.0$^{2,4}$]octane-3-carboxylic acid amide; (1R,2R,4R,7R)-4,8,8-trimethyltricyclo[5.1.0.0$^{2,4}$]octane-3-carboxylic acid amide; 2,7,7-trimethyltricyclo[4.1.1.0$^{2,4}$]octane-3-carboxylic acid amide and 4,7,7-trimethyl-tricyclo[4.1.1.0$^{2,4}$]octane-3-carboxylic acid amide.

3. The compound of claim 1, wherein the compound is a compound of the Formula (III),

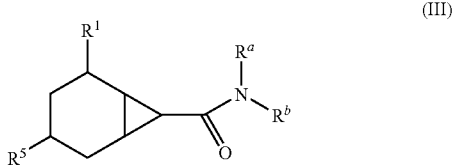

(III)

wherein:

R$^1$ and R$^5$ denote independently of one another in each case an alkyl radical with 1 to 6 C atoms or jointly denote a bridge with one or more bridge C atoms, with the exception of:

2,4-dimethylbicyclo[4.1.0]heptane-7-carboxylic acid amide, 2,7,7-trimethyltricyclo[4.1.1.0$^{2,4}$]octane-3-carboxylic acid amide and 4,7,7-trimethyl-tricyclo[4.1.1.0$^{2,4}$]octane-3-carboxylic acid amide;

or a compound of the Formula (IV)

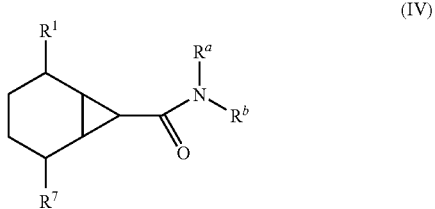

(IV)

wherein:

R$^1$ and R$^7$ denote independently of one another in each case an alkyl radical with 1 to 6 C atoms or are covalently bonded to one another, wherein in Formula (III) and Formula (IV):

R$^a$ and R$^b$ denote independently of one another hydrogen, an alkyl radical with 1 to 6 C atoms, an alkenyl radical with 2 to 6 C atoms or a cycloalkyl radical with 3 to 6 C atoms, with the exception of the compounds selected from the group consisting of:

(2S,5R)-2-isopropyl-5-methylbicyclo[4.1.0]heptane-7-carboxylic acid amide, (exo) (1R,2S,4S,5S)-tricyclo[3.2.1.0$^{2,4}$]octane-3-carboxylic acid amide and exo-tricyclo[3.2.1.0$^{2,4}$]octane-3-anti-carboxylic acid dimethyl amide.

4. The compound of claim 3, wherein R$^1$ and R$^5$ in Formula (III) as well as R$^1$ and R$^7$ in Formula (IV)

denote independently of one another in each case methyl, ethyl, n-propyl, iso-propyl, n-butyl, iso-butyl, sec-butyl, tert-butyl, n-pentyl, 1-methylbutyl, 2-methyl-butyl, 3-methylbutyl, 1,2-dimethylpropyl, 1,1-dimethyl-propyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl or 1,2,2-trimethylpropyl, or together denote a —CH$_2$—, —C(CH$_3$)$_2$—, —CH$_2$CH$_2$— or —CH═CH— bridge, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide and (exo) (1R,2S,4S,5S)-tricyclo[3.2.1.0$^{2,4}$]octane-3-carboxylic acid amide.

5. The compound of claim 3, wherein:

R$^a$ and R$^b$ denote independently of one another hydrogen or an alkyl radical with 1 to 6 C atoms, selected from the group consisting of methyl, ethyl, n-propyl, iso-propyl, n-butyl, iso-butyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethyl-propyl and 1,2,2-trimethylpropyl or an alkenyl radical with 2 to 6 C atoms or a cycloalkyl radical with 3 to 6 C atoms, with the exception of the compounds selected from the group consisting of:

2,4-dimethylbicyclo[4.1.0]heptane-7-carboxylic acid amide; (2S,5R)-2-isopropyl-5-methylbicyclo[4.1.0]heptane-7-carboxylic acid amide and (exo) (1R,2S,4S,5S)-tricyclo[3.2.1.0$^{2,4}$]octane-3-carboxylic acid amide.

6. The compound of claim 3, wherein:

R$^a$ denotes hydrogen, and

R$^b$ denotes an alkyl radical with 1 to 6 C atoms, selected from the group consisting of methyl, ethyl, n-propyl, iso-propyl, n-butyl, iso-butyl, sec-butyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethyl-1-methylpropyl, 1-ethyl-2-methylpropyl, 1,1,2-trimethylpropyl and 1,2,2-trimethylpropyl, or an alkenyl radical with 2 to 6 C atoms or a cycloalkyl radical with 3 to 6 atoms, or R$^a$ and R$^b$ both denote methyl.

7. The compound of claim 3, wherein the compound of the Formula (IV) is a compound of the Formula (IVa)

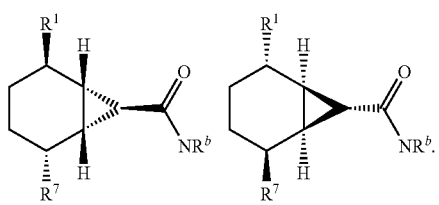
(IVa)
8. The compound of claim 3, wherein the compound of the Formula (IV) is a compound of the Formula (IVc)
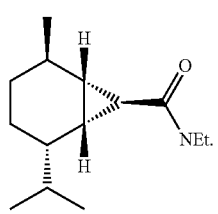
(IVc)
9. The compound of claim 3, wherein the compound of the Formula (IV) is a compound of the Formula (E1) and/or (E2)
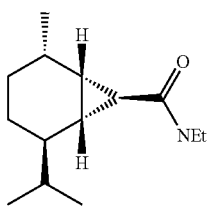
(E1)
(E2)
and/or (B1) and/or (B2)
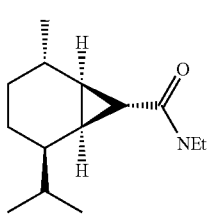
(B1)
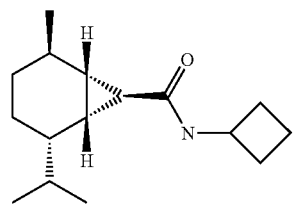
(B2)
and/or (P1) and/or (P2)
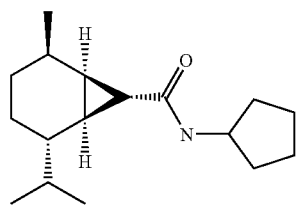
(P1)
(P2)
and/or (P3) and/or (P4)
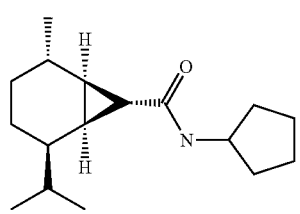
(P3)
(P4)
and/or (H1) and/or (H2)
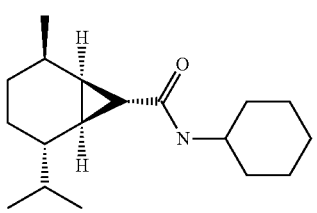
(H1)

-continued
(H2)
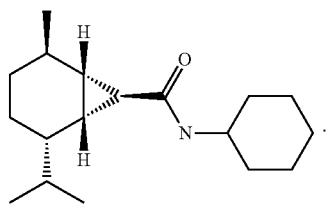
10. The compound according to claim 7, wherein the compound of Formula (IV) is one of the two enantiomeric compounds of the Formula (IVa)
(IVa)
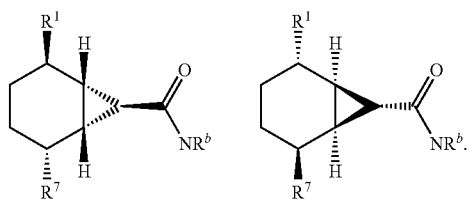
* * * * *